United States Patent
Foley et al.

(10) Patent No.: US 7,559,322 B2
(45) Date of Patent: *Jul. 14, 2009

(54) NEBULIZER APPARATUS AND METHOD

(75) Inventors: Martin P. Foley, London (CA); Jerry Grychowski, Lake Zurich, IL (US); Rick Blacker, London (CA)

(73) Assignee: Trudell Medical International, London, Ontario (CA)

(*) Notice: Subject to any disclaimer, the term of this patent is extended or adjusted under 35 U.S.C. 154(b) by 507 days.

This patent is subject to a terminal disclaimer.

(21) Appl. No.: 11/280,938

(22) Filed: Nov. 15, 2005

(65) Prior Publication Data

US 2006/0157052 A1    Jul. 20, 2006

Related U.S. Application Data

(63) Continuation of application No. 10/306,886, filed on Nov. 27, 2002, now Pat. No. 6,994,083.

(60) Provisional application No. 60/345,173, filed on Dec. 21, 2001.

(51) Int. Cl.
| | |
|---|---|
| A61M 11/00 | (2006.01) |
| A61M 16/00 | (2006.01) |
| A61M 16/10 | (2006.01) |
| A61M 15/00 | (2006.01) |

(52) U.S. Cl. .................. 128/200.14; 128/203.12; 128/203.15; 128/203.25

(58) Field of Classification Search .......... 128/200.14, 128/200.18, 200.21, 200.22; 239/338, 102.1, 239/102.2
See application file for complete search history.

(56) References Cited

U.S. PATENT DOCUMENTS

| | | | |
|---|---|---|---|
| 2,535,844 | A | 12/1950 | Emerson |
| 2,882,026 | A | 4/1959 | Eichelman |
| 2,951,644 | A | 9/1960 | Mahon et al. |
| 3,172,406 | A | 3/1965 | Bird et al. |
| 3,269,665 | A | 8/1966 | Cheney |

(Continued)

FOREIGN PATENT DOCUMENTS

DE    28 04 852    8/1978

(Continued)

OTHER PUBLICATIONS

U.S. Appl. No. 10/101,554, filed Mar. 19, 2002 and entitled "Nebulizer Apparatus and Method".

(Continued)

*Primary Examiner*—Justine R Yu
*Assistant Examiner*—Annette F Dixon
(74) *Attorney, Agent, or Firm*—Brinks Hofer Gilson & Lione

(57) ABSTRACT

A nebulizer for efficiently and reliably delivering aerosolized fluid to an inhaling patient is disclosed. The nebulizer includes a fluid channel air inlet and fluid channel air inlet valve responsive to either a manual force external of the nebulizer, or a patient's breathing, to begin the nebulization process. Also provided is a method of providing nebulization including the steps of moving a fluid channel air inlet valve against a fluid channel air inlet so that a negative pressure may build up over the fluid in the fluid channel to draw fluid from the fluid reservoir and begin nebulization during inhalation.

22 Claims, 15 Drawing Sheets

U.S. PATENT DOCUMENTS

| | | | |
|---|---|---|---|
| 3,467,092 A | 9/1969 | Bird et al. | |
| 3,490,697 A | 1/1970 | Best, Jr. | |
| 3,580,249 A | 5/1971 | Takaoka | |
| 3,584,621 A | 6/1971 | Bird et al. | |
| 3,630,196 A | 12/1971 | Bird et al. | |
| 3,658,059 A | 4/1972 | Steil | |
| 3,664,337 A | 5/1972 | Lindsey et al. | |
| 3,826,255 A | 7/1974 | Havstad et al. | |
| 3,838,686 A | 10/1974 | Szekely | |
| 3,874,379 A | 4/1975 | Enfield et al. | |
| 3,903,884 A | 9/1975 | Huston et al. | |
| 3,990,442 A | 11/1976 | Patneau | |
| 4,093,124 A | 6/1978 | Morane et al. | |
| 4,094,317 A | 6/1978 | Wasnich | |
| 4,106,503 A | 8/1978 | Rosenthal et al. | |
| 4,116,387 A | 9/1978 | Kremer, Jr. et al. | |
| 4,150,071 A | 4/1979 | Pecina | |
| 4,198,969 A | 4/1980 | Virag | |
| 4,251,033 A | 2/1981 | Rich et al. | |
| 4,268,460 A | 5/1981 | Boiarski et al. | |
| 4,333,450 A | 6/1982 | Lester | |
| 4,413,784 A | 11/1983 | Dea | |
| 4,470,412 A | 9/1984 | Nowacki et al. | |
| 4,508,118 A * | 4/1985 | Toth | 128/204.26 |
| 4,509,688 A | 4/1985 | Gagne et al. | |
| 4,588,129 A | 5/1986 | Shanks | |
| 4,620,670 A | 11/1986 | Hughes | |
| 4,657,007 A | 4/1987 | Carlin et al. | |
| 4,674,491 A | 6/1987 | Brugger et al. | |
| 4,677,975 A | 7/1987 | Edgar et al. | |
| 4,746,067 A | 5/1988 | Svoboda | |
| 4,758,224 A | 7/1988 | Siposs | |
| 4,792,097 A | 12/1988 | Kremer, Jr. et al. | |
| 4,809,692 A | 3/1989 | Nowacki et al. | |
| 4,832,015 A | 5/1989 | Nowacki et al. | |
| 4,911,157 A | 3/1990 | Miller | |
| 4,984,158 A | 1/1991 | Hillsman | |
| 5,020,527 A | 6/1991 | Dessertine | |
| 5,020,530 A | 6/1991 | Miller | |
| 5,054,477 A | 10/1991 | Terada et al. | |
| 5,054,478 A | 10/1991 | Grychowski et al. | |
| 5,078,131 A | 1/1992 | Foley | |
| 5,086,765 A | 2/1992 | Levine | |
| 5,165,392 A | 11/1992 | Small | |
| 5,167,506 A | 12/1992 | Kilis et al. | |
| 5,170,782 A | 12/1992 | Kocinski | |
| 5,241,954 A | 9/1993 | Glenn | |
| 5,277,175 A | 1/1994 | Riggs et al. | |
| 5,280,784 A | 1/1994 | Kohler | |
| 5,299,565 A | 4/1994 | Brown | |
| 5,301,662 A | 4/1994 | Bagwell et al. | |
| 5,301,663 A | 4/1994 | Small, Jr. | |
| 5,309,900 A | 5/1994 | Knoch et al. | |
| 5,312,046 A | 5/1994 | Knoch et al. | |
| 5,318,015 A | 6/1994 | Mansson et al. | |
| 5,349,947 A | 9/1994 | Newhouse et al. | |
| 5,363,842 A | 11/1994 | Mishelevich et al. | |
| 5,392,648 A | 2/1995 | Robertson | |
| 5,398,714 A | 3/1995 | Price | |
| 5,458,136 A | 10/1995 | Jaser et al. | |
| 5,461,695 A * | 10/1995 | Knoch | 392/394 |
| 5,479,920 A | 1/1996 | Piper et al. | |
| 5,487,378 A | 1/1996 | Robertson et al. | |
| 5,505,192 A | 4/1996 | Samiotes et al. | |
| 5,505,193 A | 4/1996 | Ballini et al. | |
| 5,511,538 A | 4/1996 | Haber et al. | |
| 5,511,539 A * | 4/1996 | Lien | 128/200.21 |
| 5,515,842 A | 5/1996 | Ramseyer et al. | |
| 5,520,166 A | 5/1996 | Ritson et al. | |
| 5,533,497 A | 7/1996 | Ryder | |
| 5,533,501 A | 7/1996 | Denyer | |
| 5,544,647 A | 8/1996 | Jewett et al. | |
| 5,549,102 A | 8/1996 | Lintl et al. | |
| 5,570,682 A | 11/1996 | Johnson | |
| 5,584,285 A | 12/1996 | Salter et al. | |
| 5,613,489 A | 3/1997 | Miller et al. | |
| 5,617,844 A | 4/1997 | King | |
| 5,622,162 A | 4/1997 | Johansson et al. | |
| 5,630,409 A | 5/1997 | Bono et al. | |
| 5,687,912 A | 11/1997 | Denyer | |
| 5,701,886 A | 12/1997 | Ryatt | |
| 5,752,505 A | 5/1998 | Ohki et al. | |
| 5,792,057 A | 8/1998 | Rubsamen et al. | |
| 5,803,078 A | 9/1998 | Brauner | |
| 5,823,179 A | 10/1998 | Grychowski et al. | |
| 5,875,774 A | 3/1999 | Clementi et al. | |
| 6,026,807 A * | 2/2000 | Puderbaugh et al. | 128/200.23 |
| 6,044,841 A | 4/2000 | Verdun et al. | |
| 6,116,233 A | 9/2000 | Denyer et al. | |
| 6,129,080 A | 10/2000 | Pitcher et al. | |
| 6,131,568 A | 10/2000 | Denyer et al. | |
| 6,179,164 B1 | 1/2001 | Fuchs | |
| 6,223,745 B1 | 5/2001 | Hammarlund et al. | |
| 6,237,589 B1 | 5/2001 | Denyer et al. | |
| 6,450,163 B1 | 9/2002 | Blacker et al. | |
| 6,543,448 B1 | 4/2003 | Smith et al. | |
| 6,557,549 B2 | 5/2003 | Schmidt et al. | |
| 6,584,971 B1 * | 7/2003 | Denyer et al. | 128/203.14 |
| 6,595,203 B1 * | 7/2003 | Bird | 128/200.21 |
| 6,606,992 B1 * | 8/2003 | Schuler et al. | 128/203.15 |
| 6,612,303 B1 | 9/2003 | Grychowski et al. | |
| 6,644,304 B2 | 11/2003 | Grychowski et al. | |
| 6,748,945 B2 | 6/2004 | Grychowski et al. | |
| 6,848,443 B2 * | 2/2005 | Schmidt et al. | 128/200.23 |
| 6,929,003 B2 | 8/2005 | Blacker et al. | |
| 6,994,083 B2 * | 2/2006 | Foley et al. | 128/200.14 |
| 7,051,731 B1 | 5/2006 | Rogerson | |
| 7,080,643 B2 | 7/2006 | Grychowski et al. | |
| 7,261,102 B2 | 8/2007 | Barney et al. | |
| 2001/0032643 A1 | 10/2001 | Hochrainer et al. | |
| 2002/0020762 A1 | 2/2002 | Selzer et al. | |
| 2002/0157663 A1 | 10/2002 | Blacker et al. | |
| 2003/0005929 A1 | 1/2003 | Grychowski et al. | |
| 2003/0015193 A1 | 1/2003 | Grychowski et al. | |
| 2003/0136399 A1 | 7/2003 | Foley et al. | |
| 2004/0031485 A1 | 2/2004 | Rustad et al. | |
| 2004/0060556 A1 | 4/2004 | Halamish | |
| 2004/0173209 A1 | 9/2004 | Grychowski et al. | |
| 2004/0231665 A1 | 11/2004 | Lieberman et al. | |
| 2005/0183718 A1 | 8/2005 | Wuttke et al. | |
| 2005/0205085 A1 | 9/2005 | Blacker et al. | |
| 2007/0023036 A1 | 2/2007 | Grychowski et al. | |

FOREIGN PATENT DOCUMENTS

| | | |
|---|---|---|
| DE | 199 02 847 C1 | 5/2000 |
| EP | 0 414 536 A2 | 2/1991 |
| EP | 0 587 380 B1 | 3/1993 |
| EP | 0587380 | 3/1994 |
| EP | 0 641 570 A1 | 3/1995 |
| EP | 0 711 609 A3 | 10/1996 |
| EP | 0 855 224 A2 | 7/1998 |
| EP | 0 855 224 A3 | 7/1999 |
| EP | 0 938 906 A2 | 9/1999 |
| EP | 0 855 224 B1 | 5/2004 |
| FR | 1 070 292 | 7/1954 |
| GB | 497530 | 12/1939 |
| GB | 675524 | 7/1952 |
| GB | 1 598 081 | 9/1981 |
| GB | 2 253 200 A | 9/1992 |
| WO | WO 98/26828 | 6/1998 |
| WO | WO 98/41265 | 9/1998 |

| WO | WO 99/40959 | 8/1999 |

OTHER PUBLICATIONS

International Search Report for PCT/IB 02/05524 dated May 20, 2003.

Photographs of nebulizer manufactured by PARI GmbH with detachable gas flow interrupter believed to have been publicly available prior to Feb. 13, 1996.

PARI LC PLUS Instructions for Use (GB), PARI GmbH, dated Jul. 2001.

European Search Report for Application No. 06020172.0-1526 dated Apr. 17, 2007.

* cited by examiner

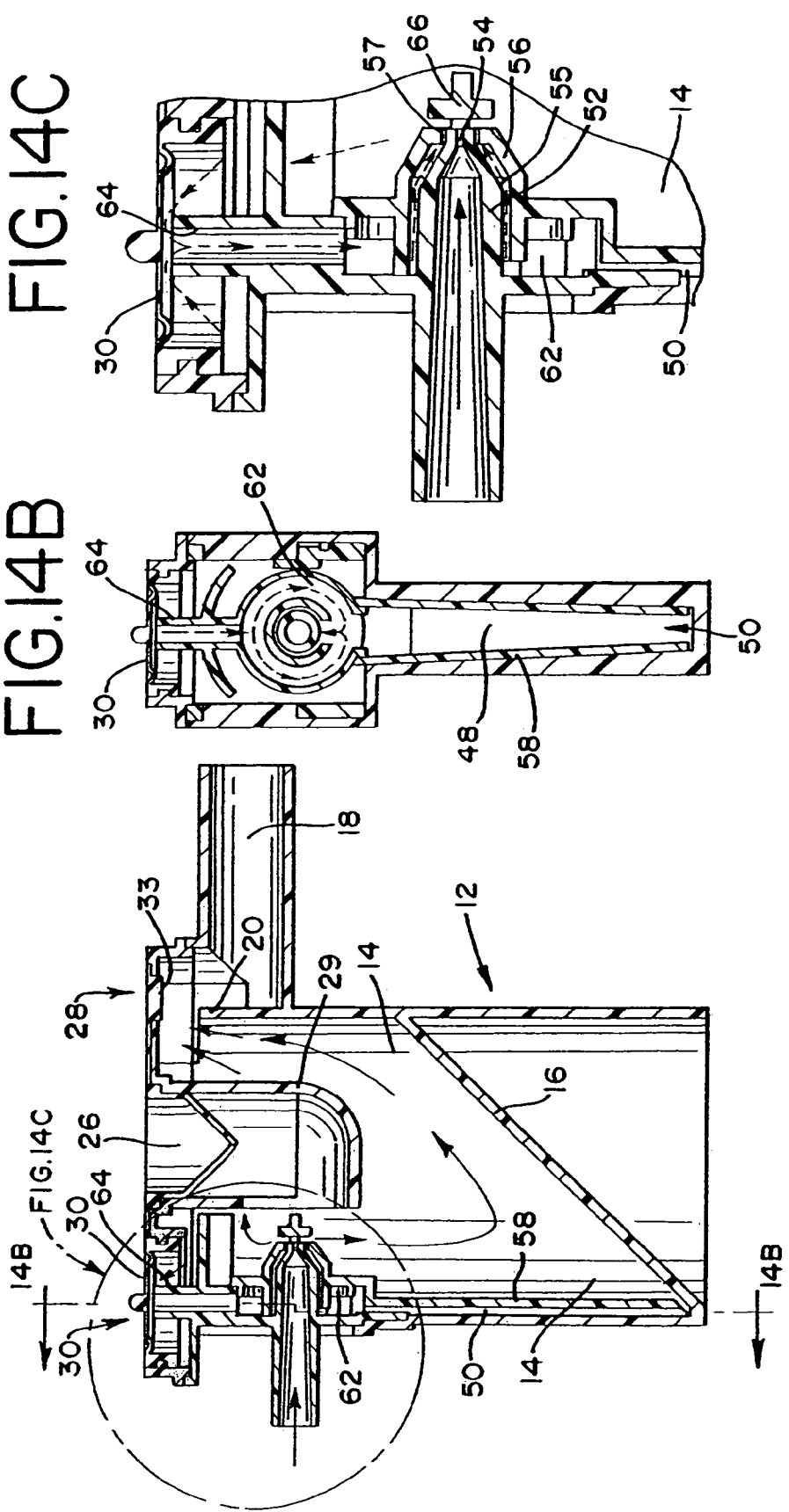

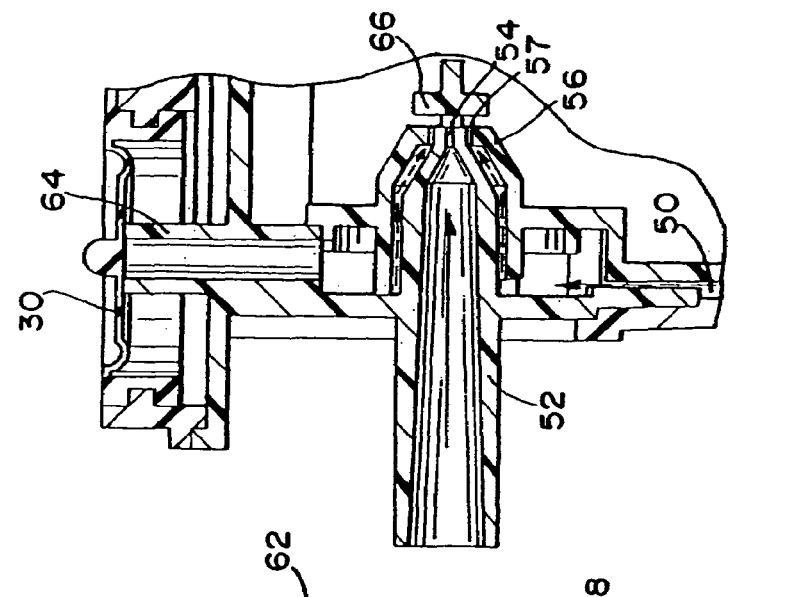
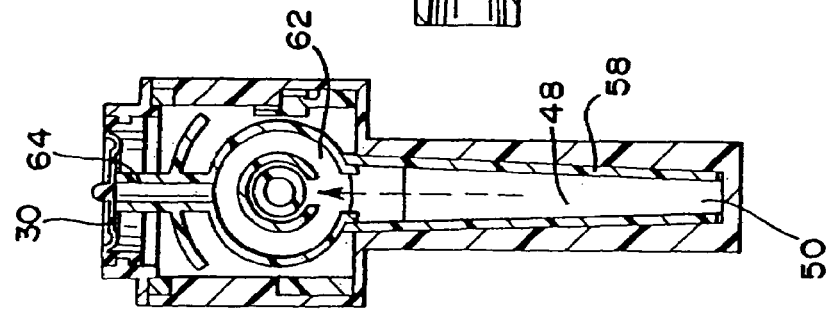
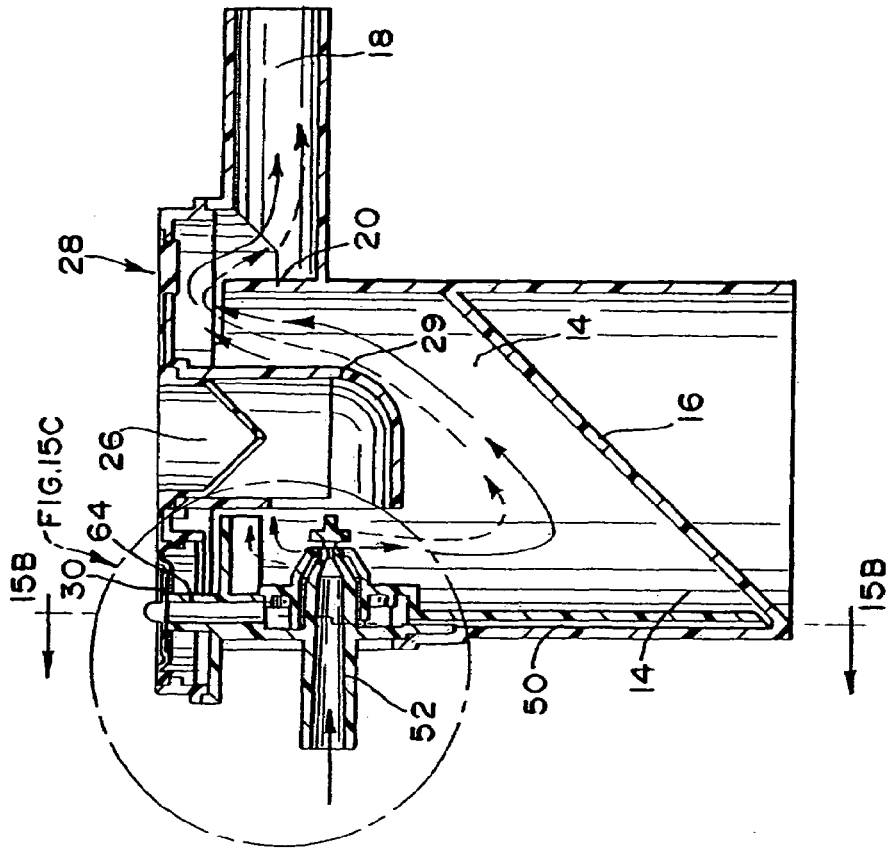

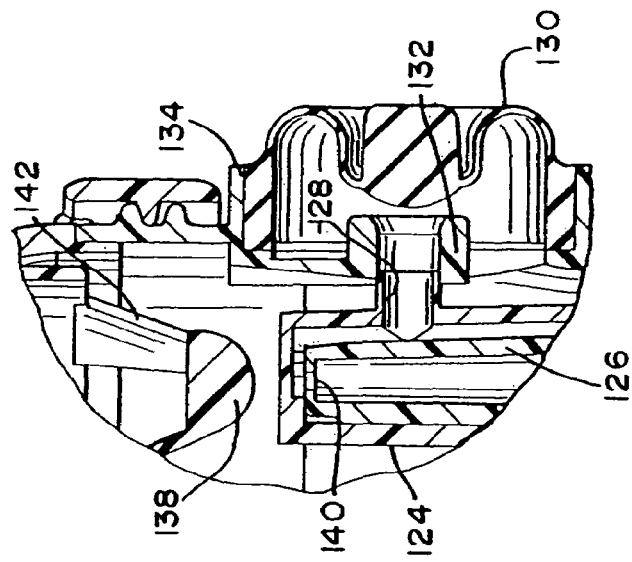
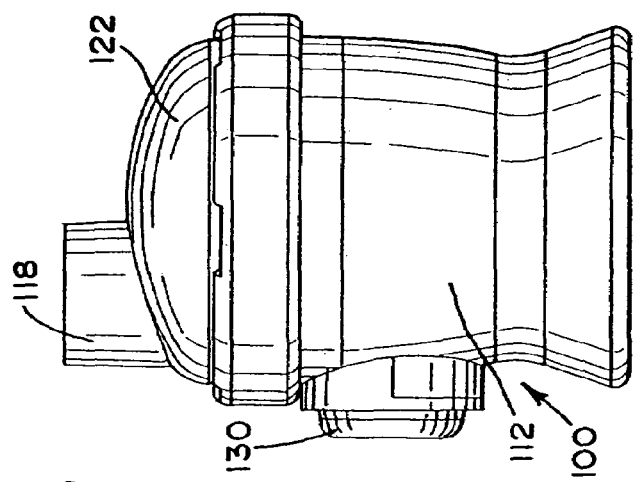
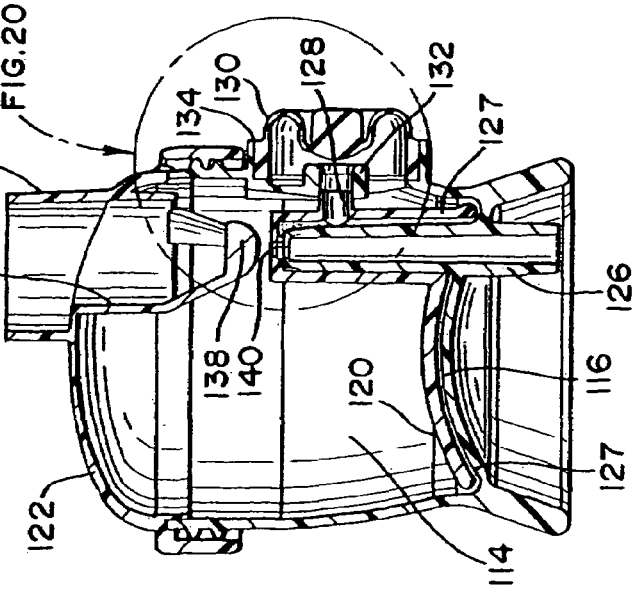

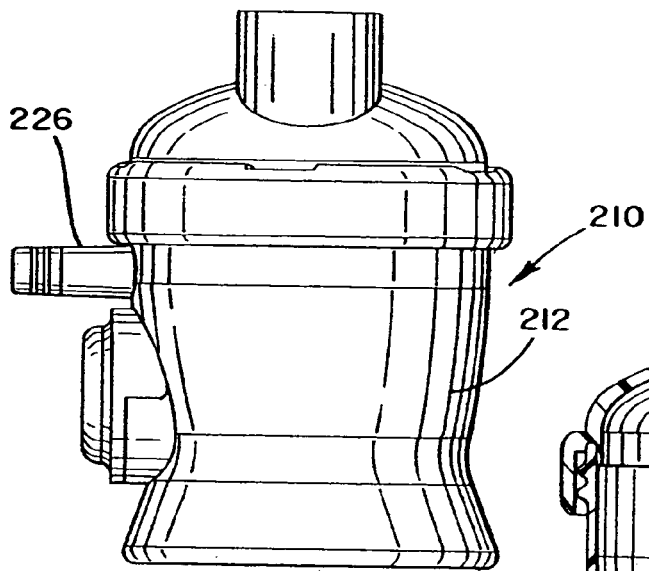
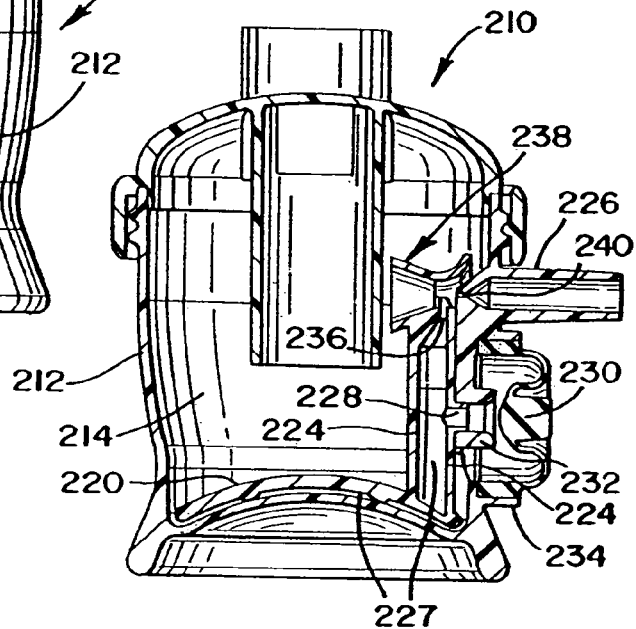
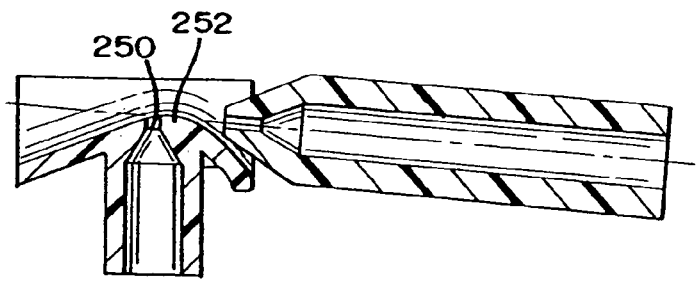
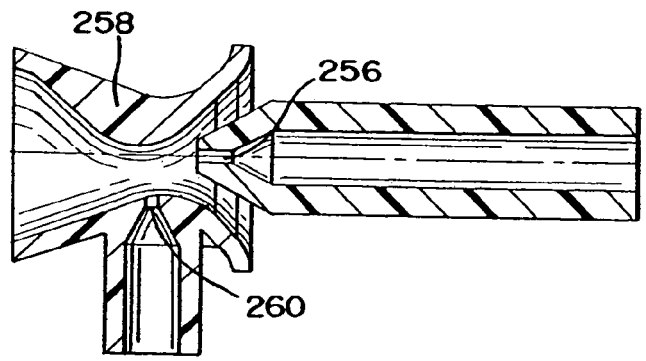

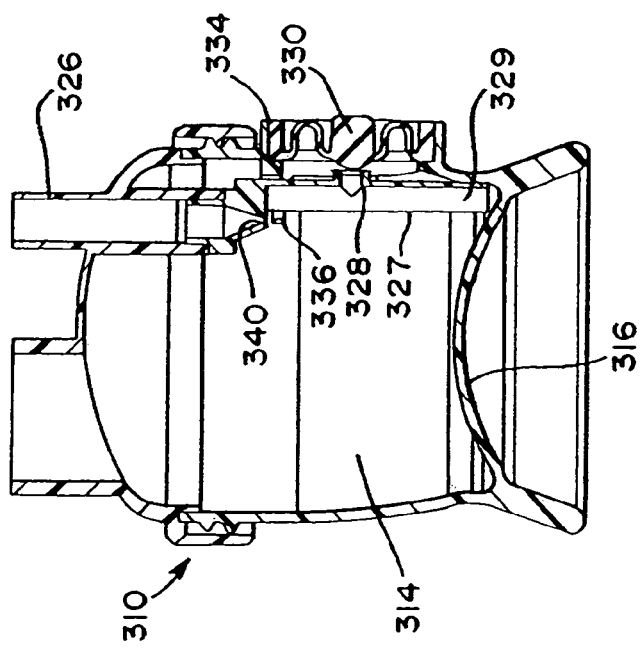
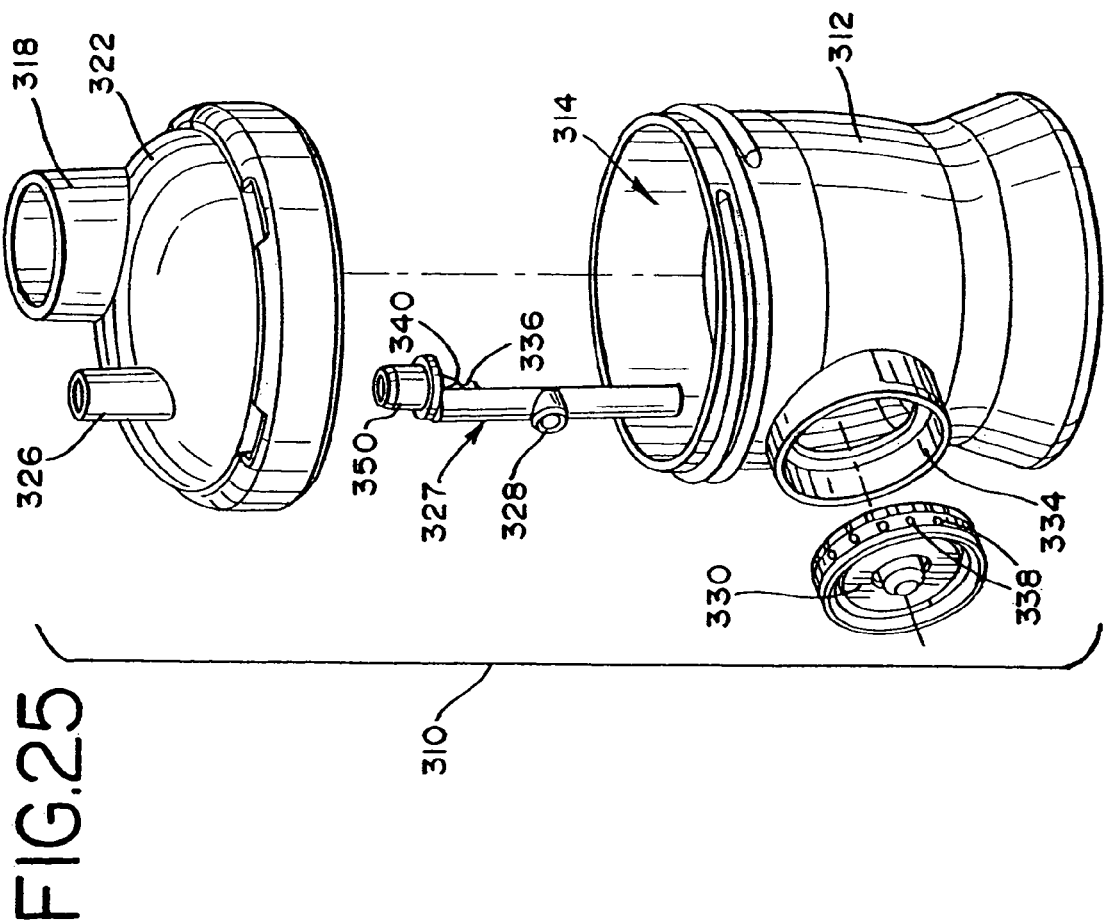

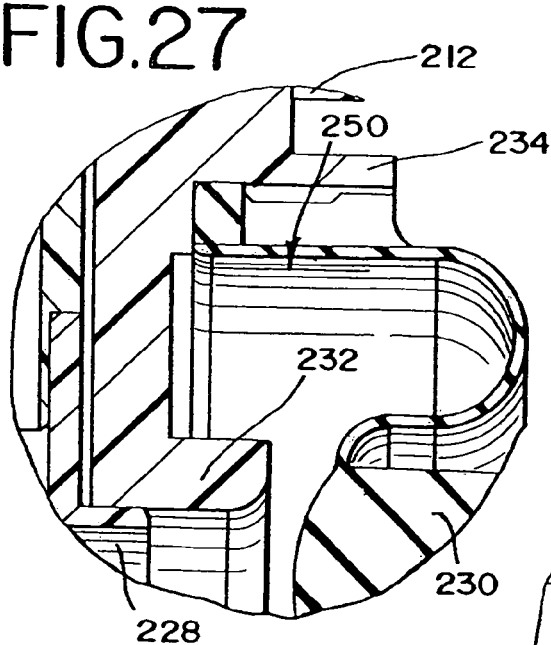
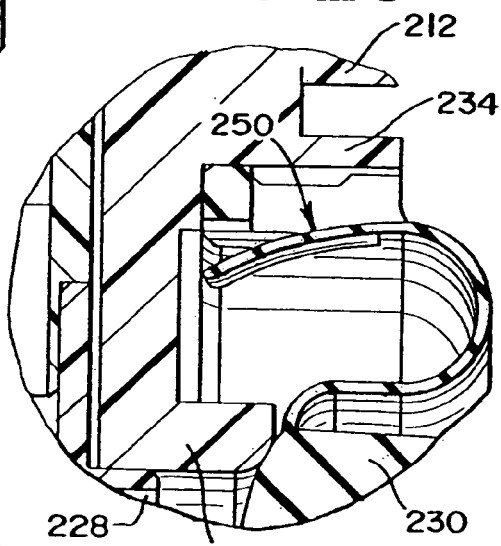
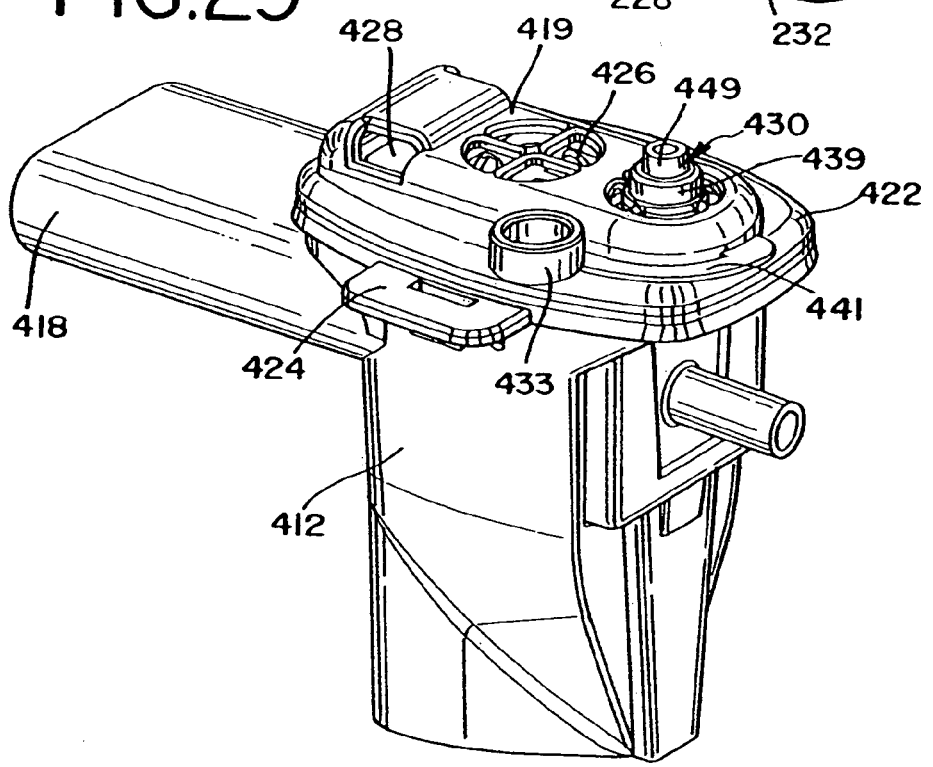

NEBULIZER APPARATUS AND METHOD

CROSS-REFERENCE

This application is a continuation of U.S. application Ser. No. 10/306,886, filed Nov. 27, 2002, now U.S. 6,994,083, which claims the benefit of U.S. application Ser. No. 60/345,173 entitled "Nebulizer Apparatus and Method" filed Dec. 21, 2001, and the entirety of each of these applications is incorporated herein by reference.

FIELD OF THE INVENTION

The present invention relates to an apparatus and method for generating an aerosol for delivery to a patient. More particularly, the present invention relates to a nebulizer configured to generate an aerosol in coordination with a patient's breathing. The present invention is also well suited for continuously generating an aerosol independent of a patient's breathing.

BACKGROUND

Medical nebulizers that nebulize a fluid into an aerosol for inhalation by a patient are well-known devices commonly used for the treatment of certain conditions and diseases. Nebulizers have applications for conscious, spontaneously-breathing patients and for controlled, ventilated patients. As used in this specification, the term "patient" includes, without limitation, humans and animals.

In nebulizers, a diverter is primarily used to direct a gas across a liquid channel to create a venturi effect causing the liquid to be entrained into the gas stream. The term "diverter", as used in this specification, includes, without limitation, any baffle or impinger. As a result of the nebulization process described above, the fluid is transformed into an aerosol, that is, the fluid is caused to form small particles that are suspended in the air and that have a particle size in a range suitable for the intended therapy. A common therapy is inhalation therapy, whereby a patient inhales a medicated aerosol to treat an ailment, such as asthma.

Important considerations in the design of a nebulizer are the timing and dosage regulation of the aerosolized fluid. In some nebulizer designs, a continuous stream of pressurized gas entrains the fluid against the diverter to constantly generate an aerosol until the fluid in a reservoir is depleted. Continuous nebulization may result in a waste of aerosol during a patient's exhalation or during a delay between inhalation and exhalation. The amount of wasted aerosol may be difficult to quantify and some of the aerosol may be lost to condensation on the nebulizer or mouthpiece during periods of non-inhalation. Nebulizers implementing a timed or non-continuous nebulization may adversely affect particle size and density as the nebulization is turned on and off.

Effective and economical nebulizer therapy includes the ability to quickly generate an aerosol within a desired particle size range. An effective nebulizer preferably provides these features synchronously with the inhalation of the patient. In order to actuate a mechanical nebulizer, a patient's inhalation effort must overcome certain variables. Depending on the structural configuration of the nebulizer, these variables may include one or more of the following: the volumetric flow rate of the flowing gas; air leaks in the device; the force exerted by the flowing gas on a moveable diverter; and the friction between moveable parts. The greater the flow rate, air leaks and friction, the greater the inhalation effort required in order to actuate the device. It is desirable that a nebulizer have adequate sensitivity to quickly respond to an inhalation while not adversely restricting the patient's inhalation.

Nebulizer designs in use today often consist of ten or more separate parts that may require expensive and time consuming manufacturing and assembly techniques. Accordingly, it is also desirable to have a nebulizer that is inexpensive to manufacture and assemble.

BRIEF SUMMARY

In order to address the deficiencies in the prior art and provide improved performance, a nebulizer and method are provided. According to a first aspect of the invention, a nebulizer is provided with a housing having an ambient air inlet and a chamber for holding an aerosol. An air outlet communicates with the chamber for permitting the aerosol to be withdrawn from the chamber. A fluid orifice is adjacent a pressurized gas inlet, where the pressurized gas inlet is in communication with the chamber and where the fluid orifice is in communication with a fluid channel. In one preferred embodiment, the fluid orifice is preferably positioned at the opposite end of a nozzle cover from a fluid inlet, wherein the fluid inlet is capable of fluid communication with a reservoir. A diverter is positioned in the chamber adjacent to the pressurized gas inlet wherein pressurized gas from the pressurized gas outlet is diverted over the fluid orifice. A fluid channel air inlet valve is movably disposed across a fluid channel air inlet, where the fluid channel air inlet is in communication with the fluid channel and the fluid orifice.

In one embodiment, the fluid channel air inlet valve may be a flexible membrane responsive to inhalation or physical contact to seal the fluid channel air inlet and permit a negative pressure over fluid in the fluid reservoir to be drawn to the fluid orifice. As used in this specification, the term "fluid orifice" means either the fluid inlet or the fluid outlet and may be used interchangeably with these terms. The nebulizer may have an actuator piston connected with at least a portion of a nozzle cover to move all or part of the fluid orifice, or all or part of the fluid pathway between the reservoir of fluid and the fluid orifice. Additionally, the ambient air inlet valve may be used to alleviate inhalation effort after an initial period of inhalation. The diverter may also be movable relative to the nebulizer housing, but fixedly positioned relative to either the pressurized gas orifice or fluid orifice. In yet other embodiments the fluid channel air inlet valve may be a duck-bill valve or an umbrella valve. The fluid channel air inlet may be integrally formed out of a single piece of material that also contains an exhalation valve and an ambient air inlet valve for the nebulizer. Other embodiments may include a cap, discrete or integrally formed with the valves via a tether, that is sized to hold down the fluid channel air inlet valve and allow continuous nebulization. A protective, substantially rigid grid may cover one or more of the valves that allows the valves to function and pass air, but that protects that valve material from inadvertent abrasion and other contamination.

According to another aspect of the invention, a method of providing a nebulized fluid to a patient includes providing a nebulizer having a diverter fixedly positioned with respect to a pressurized gas orifice in a chamber, a fluid reservoir in communication with the chamber, and a fluid channel air inlet valve responsive to a pressure change in the chamber to seal a fluid channel air inlet. Upon inhalation through an air outlet connected to the chamber, the fluid channel air inlet valve seals against the fluid channel air inlet and a negative pressure is created over fluid in the fluid channel such that medication is drawn through the fluid orifice. Further aspects and advantages of the invention are discussed below in conjunction with the preferred embodiments.

BRIEF DESCRIPTION OF THE DRAWINGS

FIG. 1 is perspective view of a nebulizer according to one embodiment of the present invention.

FIG. 2 is a cross-sectional view of the nebulizer of FIG. 1.

FIG. 14A is a cross-sectional view of the nebulizer of FIG. 1 illustrating the flow of gas and the position of the valves when the nebulizer is at rest in a non-actuated position.

FIG. 14B is a cross-sectional view of the nozzle system of the nebulizer of FIG. 14A.

FIG. 14C is a partial enlarged view of the nebulizer of FIG. 14A.

FIG. 15A is a cross-sectional view of the nebulizer of FIG. 1 illustrating the flow of gas and aerosol and the position of the valves at the start of inhalation when the nebulizer is actuated.

FIG. 15B is a cross-sectional view of the nozzle system of the nebulizer of FIG. 15A.

FIG. 15C is a partial enlarged view of the nebulizer of FIG. 15A.

FIG. 18 is a cross-sectional view of the nebulizer of FIG. 17.

FIG. 19 is a side view of the nebulizer of FIG. 17.

FIG. 20 is a magnified view of a portion of the nebulizer of FIG. 18.

FIG. 21 is a side view of a second alternative embodiment of the nebulizer of FIG. 1

FIG. 22 is cross-sectional view of the nebulizer of FIG. 21.

FIG. 23 is a cross-sectional view of an alternative gas orifice and diverter orientation.

FIG. 24 is a cross-sectional view of a second alternative gas orifice and diverter orientation.

FIG. 25 is an exploded view of an alternative embodiment of the nebulizer of FIG. 22.

FIG. 26 is a cross-sectional view of the assembled nebulizer of FIG. 25.

FIG. 27 is a partial cross-section of the fluid channel air inlet valve during exhalation.

FIG. 28 is a partial cross-section of the valve of FIG. 27 during inhalation.

FIG. 29 is a perspective view of an alternative embodiment of the nebulizer of FIGS. 1-4.

DETAILED DESCRIPTION OF THE PRESENTLY PREFERRED EMBODIMENTS

Figures 1, 2:
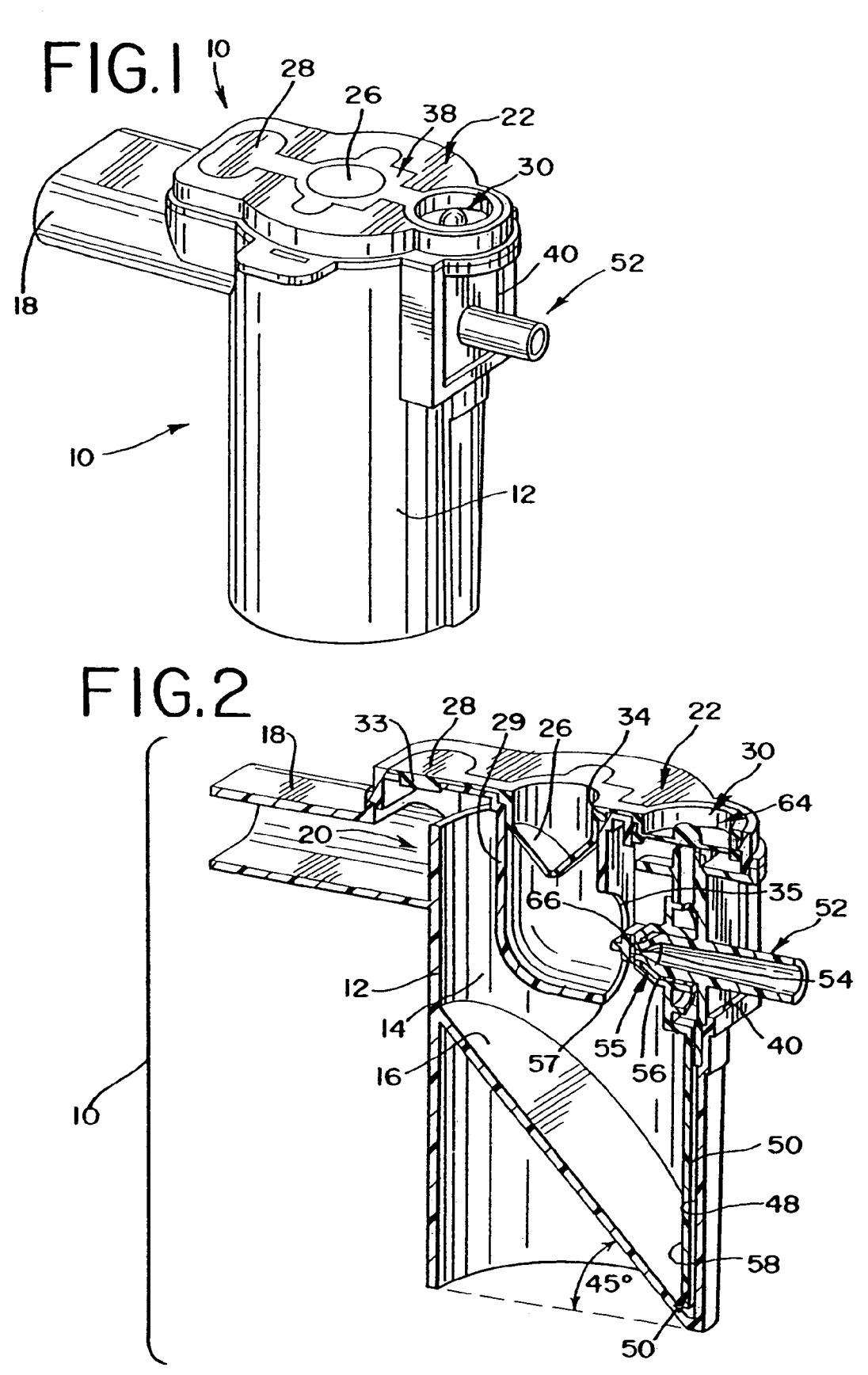
Figure 4:
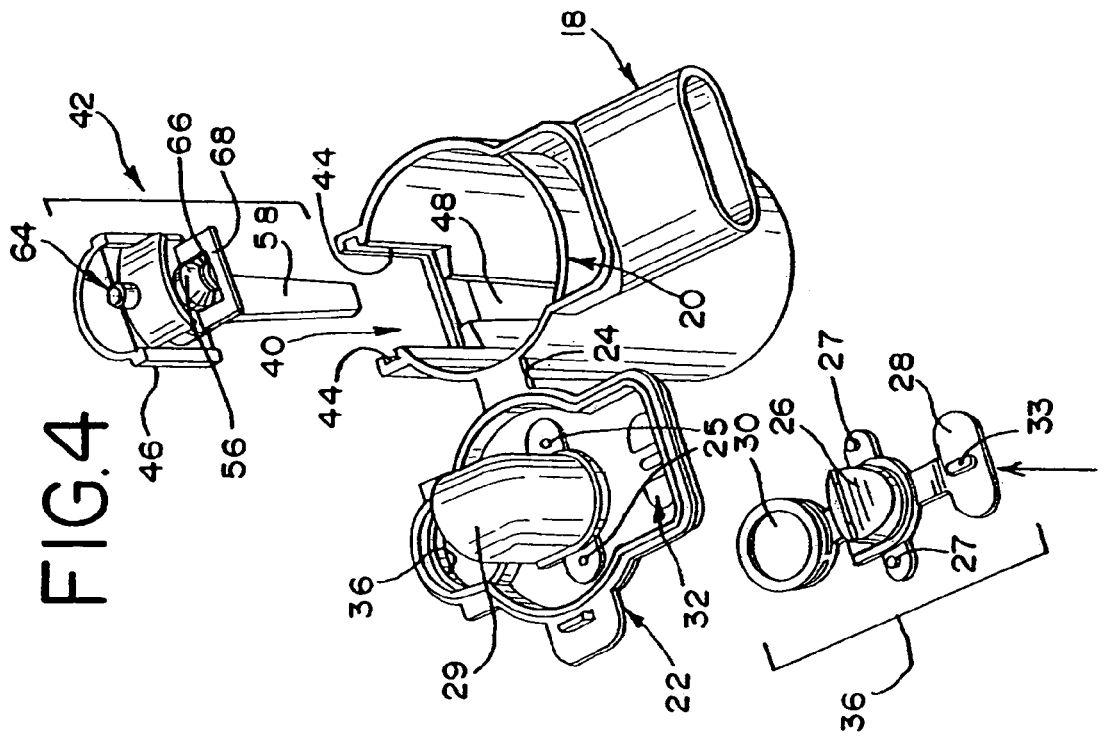
FIG. 4 is an exploded perspective view of the nebulizer of FIG. 1.

A preferred embodiment of a nebulizer 10 for nebulizing a fluid is shown in FIGS. 1-4. As used in this specification, the term "fluid" includes, without limitation, a fluid comprising a medicine, whether in the form of an emulsion, suspension or solution, that can be nebulized into an aerosol.

The nebulizer includes a housing 12 consisting of a chamber 14 that is suited to receive and hold a fluid. The chamber is preferably substantially cylindrical, however any of a number of shapes may be used. The chamber 14 includes an angled bottom portion 16 so that any fluid in the chamber will be directed toward one region of the bottom of the chamber to facilitate removal of all the fluid. In one embodiment, the bottom portion 16 is set at an approximate 45 degree angle in order to reduce wastage by maximizing the amount of fluid that is evacuated from the chamber for nebulization. An air outlet 18 extends away from the housing 12 and communicates with the chamber 14. A barrier 20 on the housing forces any aerosol generated in the chamber to flow up and over the barrier 20 before passing through the air outlet 18. The indirect path formed by the barrier and the air outlet preferably helps to limit the particle size of the aerosol that escapes the chamber 14.

Preferably, the housing is integrally formed with a lid portion 22 via a hinge 24 such that the lid portion 22 may be sealed and unsealed against the top of the housing to allow someone to fill the chamber 14 with a fluid. The lid portion 22 of the housing 12 is preferably molded as one part with the chamber 14.

The lid 22 preferably includes a group of openings suited to receive an air inlet valve 26, an exhalation valve 28 and a fluid channel air inlet valve 30, respectively. A first opening 32 is sized to accommodate the exhalation valve 28, a second opening 34 is sized to accommodate the air inlet valve 26, and the third opening 36 is sized to accommodate the fluid channel air inlet valve 30. The housing and lid may be constructed of a single piece of material formed by an injection molding process. Suitable materials include a plastic material, such as polypropylene, polycarbonate or a polycarbonate blend, or a metal material.

In a preferred embodiment, each of the air inlet valve 26, exhalation valve 28 and fluid channel air inlet valve 30 is integrally formed into a valve system 38 from a single piece of flexible material. The exhalation valve 28 preferably is mounted into the first opening 32 by a center anchor 33 so that the assembled valve and opening form a butterfly configuration allowing air to escape upon exhalation and sealing upon inhalation to prevent inhalation of air through the opening. The air inlet valve 26 preferably has a duck bill valve configuration and is mounted in the second opening 34 of the lid by two anchors 27 that cooperate with anchor openings 25 on opposite sides of the second opening 34. The duck bill configuration is oriented with the tapered portion directed into the chamber 14 so that ambient air may be drawn in upon inhalation and so that the parallel sealing members, or lips, of the valve prevent any flow of air out of the chamber upon exhalation. An ambient air guide 29 is preferably integrally formed in, or attached to, the lid portion 22. The ambient air guide 29 is disposed under the second opening 34 and the air inlet valve 26 so that distal opening 35 directs ambient air over the aerosol generating structure.

The fluid channel air inlet valve 30 preferably mounts into the third opening 36 and completely seals the third opening. Preferably, the fluid channel air inlet valve is a flexible membrane having a thickness that is sensitive to, and flexibly movable in response to, air pressure changes within the chamber 14 corresponding to inhalation and exhalation through the air outlet 18. As explained in greater detail below, the fluid channel air inlet 64 positioned inside the chamber and directly adjacent to the fluid channel air inlet valve may be sealed and unsealed synchronously with a patient's breathing or may be manually actuated by physical contact against the outside of the valve 30. In one embodiment, the material is flexible rubber material. Although individual valves may be fabricated separately on separate pieces of flexible material, or the valves may each be constructed from numerous individual components, the valve system 38 is preferably a one-piece, integrated construction reducing the part count and cost of manufacturing (including the cost of assembly).

Figure 3:
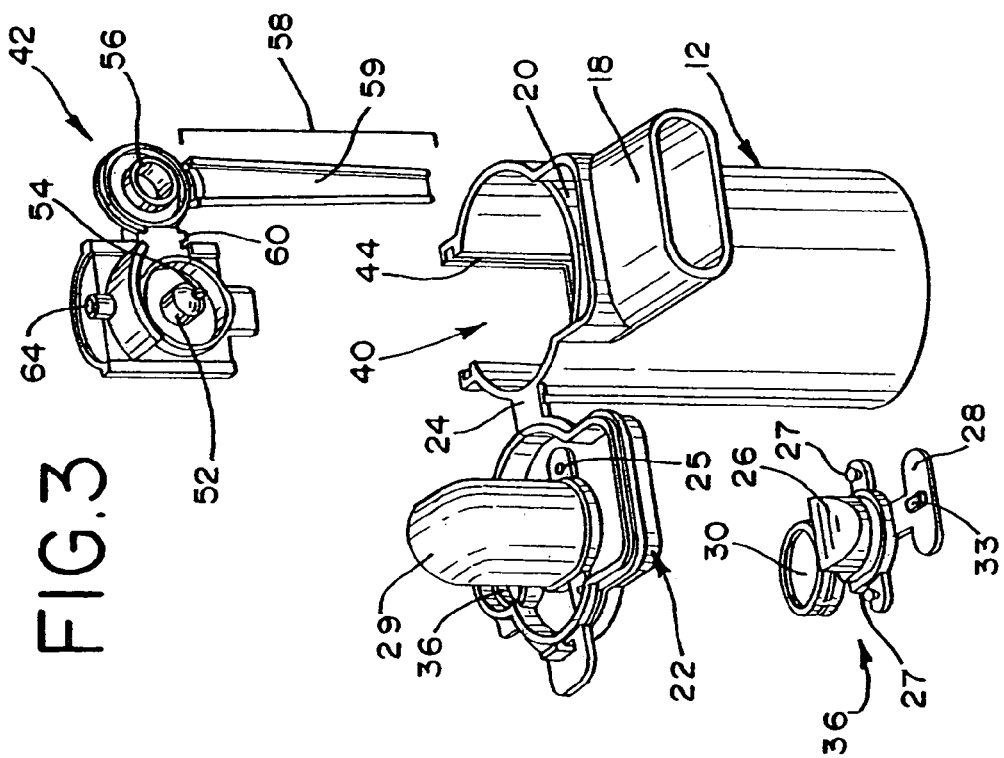
FIG. 3 is an exploded perspective view of the nebulizer of FIG. 1.

Referring to FIGS. 3-4, a portion of the chamber wall is cut-out 40 in order to accommodate the nozzle system 42. The nozzle system 42 is configured to allow for frictional or snap fit assembly onto the wall of the chamber 12. A pair of guide slots 44 on either side of the cut-out 40 cooperate with the edges 46 of the nozzle assembly 42 to provide for a snug, substantially airtight fit. A recessed channel 48 formed in the wall of the chamber 14 directly below the cut-out 40 forms part of the fluid channel 50 (FIG. 2) when the nebulizer 10 is fully assembled.

The nozzle system 42 includes a pressurized gas nozzle 52 that, when assembled with the housing 12, extends outside the chamber 14 at a proximal end and tapers down to a pressurized gas orifice 54 at a distal end positioned inside the chamber. A nozzle cover 56 and a fluid channel stem 58 are attached to the gas nozzle portion of the nozzle system 42 by a living hinge 60 (FIG. 3). When the two parts of the nozzle system 42 are closed, the nozzle cover 56 forms a fluid chamber 62 around a portion of the gas nozzle, where the fluid chamber is in fluid communication with the fluid channel stem 58 and a fluid channel air inlet 64.

A passageway 55 (FIG. 2) may be formed by a spacing between the gas nozzle 52 and nozzle cover 56, a groove in the inner circumference of the nozzle cover, a groove in the outside of the nozzle, or a combination of grooves on the outside of the nozzle and inside of the nozzle cover. The fluid orifice 57 is positioned adjacent the pressurized gas orifice 54. As illustrated in FIGS. 2 and 14C, the fluid orifice is an annular orifice defined by a gap between the inner diameter of the tip of the nozzle cover and the outer diameter of the tip of the nozzle. In one preferred embodiment, the outer diameter of the tip of the nozzle is 2 mm and the inner diameter of the nozzle cover tip is 2.46 mm. Other diameters may also be used. Although a single annular orifice is shown, embodiments where the fluid outlet has other shapes, or comprises more than one discrete orifice positioned adjacent the pressurized gas orifice, are also contemplated.

In this embodiment, the fluid channel air inlet 64 is located near the top of the chamber 14 and is substantially parallel to the longitudinal axis of the chamber 14. The distal end of the nozzle cover forms a fluid orifice such that the fluid and gas orifices 57, 55 are substantially parallel to each other. The space between the nozzle cover 56 and the pressurized gas nozzle 52 forms the fluid passageway 55 at the distal end which leads to the fluid orifice 57. A non-moveable diverter 66 is located adjacent the distal end. The diverter directs the gas across the fluid orifice 57 to create a venturi effect, thereby causing the fluid to be entrained into the gas stream to create an aerosol. Preferably, the diverter 66 is attached to, or integrally molded with, the nozzle cover 56. Alternatively, the diverter may be connected to the inside of the nebulizer 10.

Figure 5:
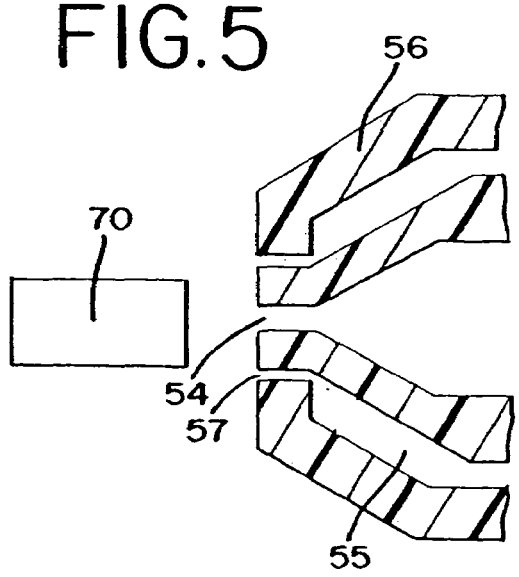
FIG. 5 is a cross-sectional view of a first alternative nozzle and diverter arrangement.
Figure 6:
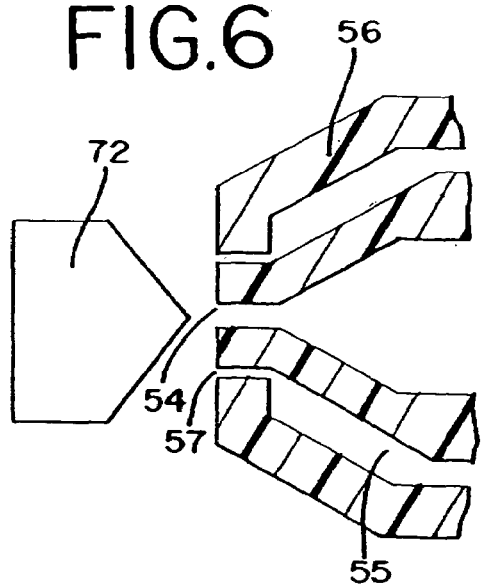
FIG. 6 is a second alternative embodiment of a first alternative nozzle and diverter arrangement.

As best shown in FIG. 4, a support beam 68 connects the diverter 66 to the nozzle system 42. Preferably, the diverter 66 has a flat surface having a predetermined area and is positioned at a fixed distance from the gas orifice 54. The diameter of the gas orifice may be varied, but is preferably 0.46 mm. In one preferred embodiment, the distance between the diverter and nozzle is in the range of 0.15 mm to 1.25 mm, and most preferably 0.75 millimeters (mm), and the width of the diverter is approximately 4.5 mm. These dimensions may be varied to achieve a desired particle size and aerosolization as is known to those of skill in the art. The surface of the diverter 66 is also preferably aligned parallel to the surface of the distal end of the gas nozzle 52 and perpendicular to the flow of pressurized gas through the gas orifice 54. Other diverter embodiments may also be implemented. For example, FIG. 5 illustrates a diverter 70 having a perpendicular surface with a width less than 4.5 mm. In other embodiments, a diverter 72 with a wedge shape or other non-perpendicular orientation may be used as shown in FIG. 6.

The fluid channel stem 58 extends substantially vertically along the longitudinal axis of the chamber 14. The stem has a carved out portion 59 which forms an enclosed lumen once it is assembled and mated with the recessed channel 48 in the chamber wall. The resulting fluid channel shape is substantially rectangular. In other embodiments, the recessed channel 48 and carved-out portion 59 of the fluid channel stem 58 may be constructed to cooperate and form any of a number of continuous or varying cross-sections along their lengths. In another embodiment, the recessed channel 48 and fluid channel stem 58 may combine to form a plurality of separate fluid channels. In one preferred embodiment, the chamber has a volume of approximately 50 milliliters (ml), with a maximum fluid fill volume of 5 ml. In this embodiment, the fluid channel length is approximately 22.8 mm.

Referring to FIGS. 1-4, the fluid channel air inlet valve 30 is a flexible membrane that on inhalation substantially seals the fluid channel air inlet 64 communicating with the fluid inlet tube. Once substantially sealed, the necessary pressure is created inside the housing in order to entrain the fluid up the fluid channel into the path of the pressurized gas causing the fluid and gas to mix resulting in an aerosol with the desired particle size characteristics. The flexible membrane is preferably very sensitive to flow and, therefore, can be triggered at low flows making the apparatus suitable for children and the elderly who typically have low rates of inhalation. Further, the membrane can also be manually depressed. Accordingly, the patient or the caregiver can manually actuate the apparatus.

Figure 7:
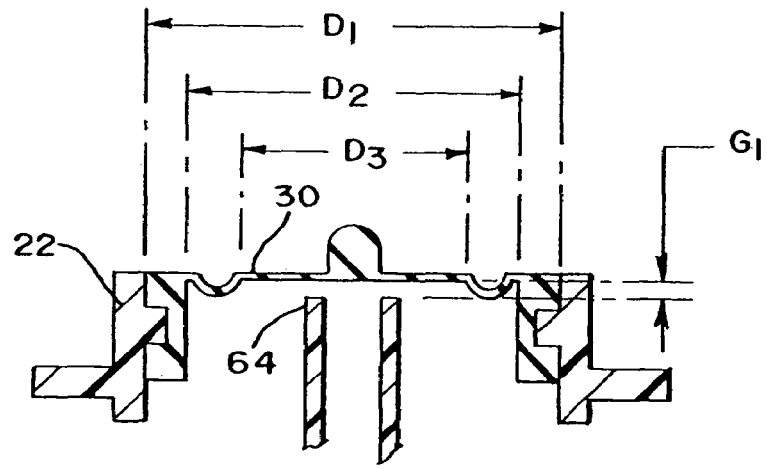
FIG. 7 is a cross-sectional view of the fluid channel air inlet valve of the embodiment of FIGS. 1-4 in a non-nebulizing position.
Figure 8:
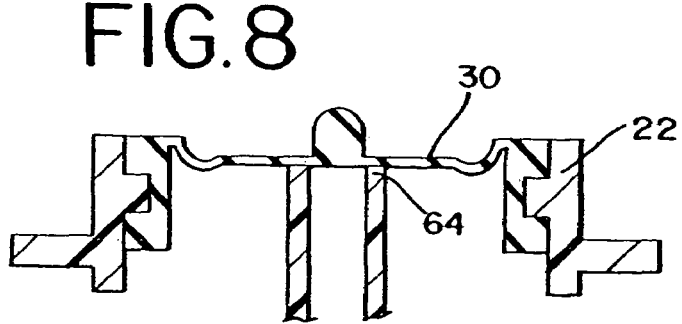
FIG. 8 is a cross-sectional view of the fluid channel air inlet valve of FIG. 4 in a nebulizing position.

Referring to FIGS. 7 and 8, in one preferred embodiment the fluid channel air inlet valve 30 is configured to deflect over a gap G, in the range of 0.5-1.0 mm, and most preferably approximately 0.75 mm, before it blocks the end of the fluid channel air inlet 64. Other gap distances may be used with variations in the parameters of the membrane, geometry and diameter, and variation in other aspects of the nebulizer such as fluid channel air inlet. FIG. 7 illustrates the spaced apart relationship that exists during exhalation or at rest, while FIG. 8 shows the fluid channel air inlet valve 30 sealing against the fluid channel air inlet during inhalation. In this embodiment, the fluid channel air inlet valve is designed to respond to a negative pressure of approximately 0.5-1.0 cm $H_2O$ to achieve this deflection. The thickness of the membrane may be approximately 0.2 mm. The outer diameter $D_1$ is 14 mm, the responsive membrane diameter $D_2$ is approximately 11 mm and the effective area of the membrane $D_3$ is approximately 6.5 mm. As shown, the area between $D_1$ and $D_2$ is used to form a grommet-type connection to hold the membrane in the opening 36 of the lid portion. The area between $D_2$ and $D_3$ functions as a rolling diaphragm to allow the membrane to move up and down in response to minimal negative pressure in the chamber. Other gap distances G, and geometries, may be utilized in other embodiments.

Figure 9:
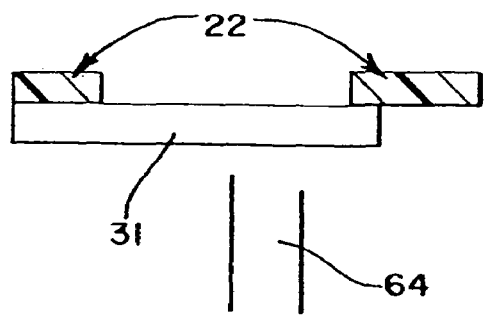
FIG. 9 is a cross-sectional view of an alternative air inlet and fluid channel air inlet valve in a non-nebulizing position.
Figure 10:
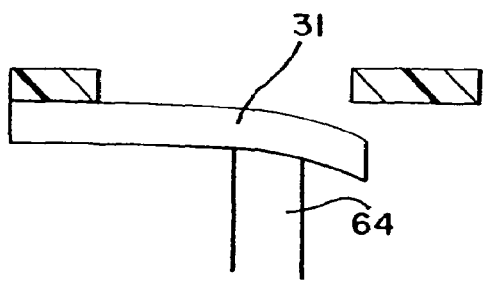
FIG. 10 is a cross-sectional view of the valve of FIG. 9 in a nebulizing position.

In one alternative embodiment, illustrated in FIGS. 9 and 10, a combination ambient air inlet valve and fluid channel air inlet valve may be used instead of separate ambient air inlet and fluid channel air inlet valves. The combination valve 31 may be constructed of a flat, flexible material that will remain closed during exhalation and at rest (FIG. 9), and flex in response to negative pressure in the chamber, or physical contact with the valve, to allow ambient air into the nebulizer and to contact and seal against a fluid channel air inlet 64 to initiate nebulization (FIG. 10). Another variation contemplated for this alternative embodiment is a rigid material connected to the container 12 or top portion 22 by a hinge having a biasing member configured to maintain the combination valve closed during exhalation and at rest, while allowing the combination valve to open at a desired negative pressure and initiate nebulization by sealing against the fluid channel air inlet. Any valve arrangement responsive to a negative pressure and positioned to seal against a fluid channel air inlet may be used. Additionally, the duck bill valve used as the ambient air inlet valve 26 in FIGS. 1-4 may also be designed to open up at a pressure in the range of 0.5-1.0 cm $H_2O$.

Although a flexible membrane and duck bill valve have been shown as the preferred fluid channel air inlet valve and ambient air inlet valve, these valves may be any type of pressure release valve that would not move or open until the negative pressure within the nebulizer reaches a desired level, in this example 0.5-1.0 cm $H_2O$. Additionally, the diameter of the fluid channel air inlet is preferably selected such that the negative pressure generated within the fluid channel when the nebulizer is at rest is less than the negative pressure necessary to draw the liquid up through the fluid channel to the liquid orifice. The exact dimensions necessary for the fluid channel air inlet are dependent on the distance from the nozzle region to the top of the liquid in the liquid reservoir. For example, if the vertical distance from the fluid orifice to the top of the liquid surface in the reservoir is 2 cm, then the negative pressure above the fluid in the fluid channel must be less than 2 cm $H_2O$ when the nebulizer is in its at rest phase.

In one preferred embodiment, the diameter of the fluid channel air inlet is 2.5 mm. In order to adjust the sensitivity of the fluid channel air inlet to a patient's breathing, the fluid channel air inlet valve may be constructed of a material or material thickness to be more responsive to changes in air pressure, the spacing between the fluid channel air inlet valve and fluid channel air inlet may be adjusted, and the diameter of the fluid channel air inlet may be selected to be of a suitable size to change the sensitivity. The diameter, thickness, geometry, and durometer of the fluid channel air inlet valve are all factors which may be selected to adjust responsiveness. Preferably, the diameter and position of the fluid channel air inlet valve is such that a patient or caregiver may also manually actuate the nebulizer by applying pressure to the valve through physical contact by hand or other object.

Figure 11A:
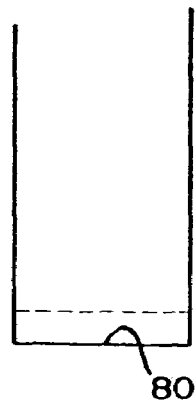
FIG. 11A illustrates a first alternative geometry of a chamber floor for use in the nebulizer of FIGS. 1-4.
Figure 11B:
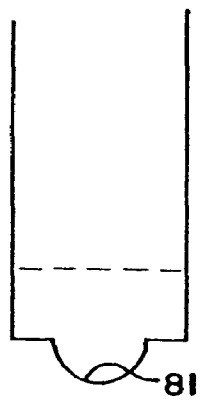
FIG. 11B illustrates a second alternative geometry of a chamber floor for use in the nebulizer of FIGS. 1-4.
Figure 12:
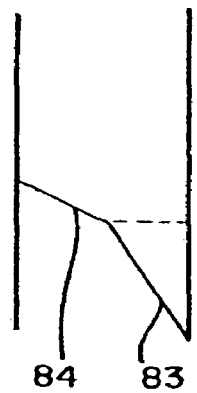
FIG. 12 illustrates a third alternative geometry of a chamber floor for use in the nebulizer of FIGS. 1-4.
Figure 13:
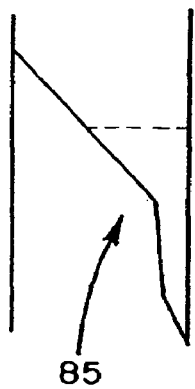
FIG. 13 illustrates a fourth alternative geometry of a chamber floor for use in the nebulizer of FIGS. 1-4.
Figure 17:
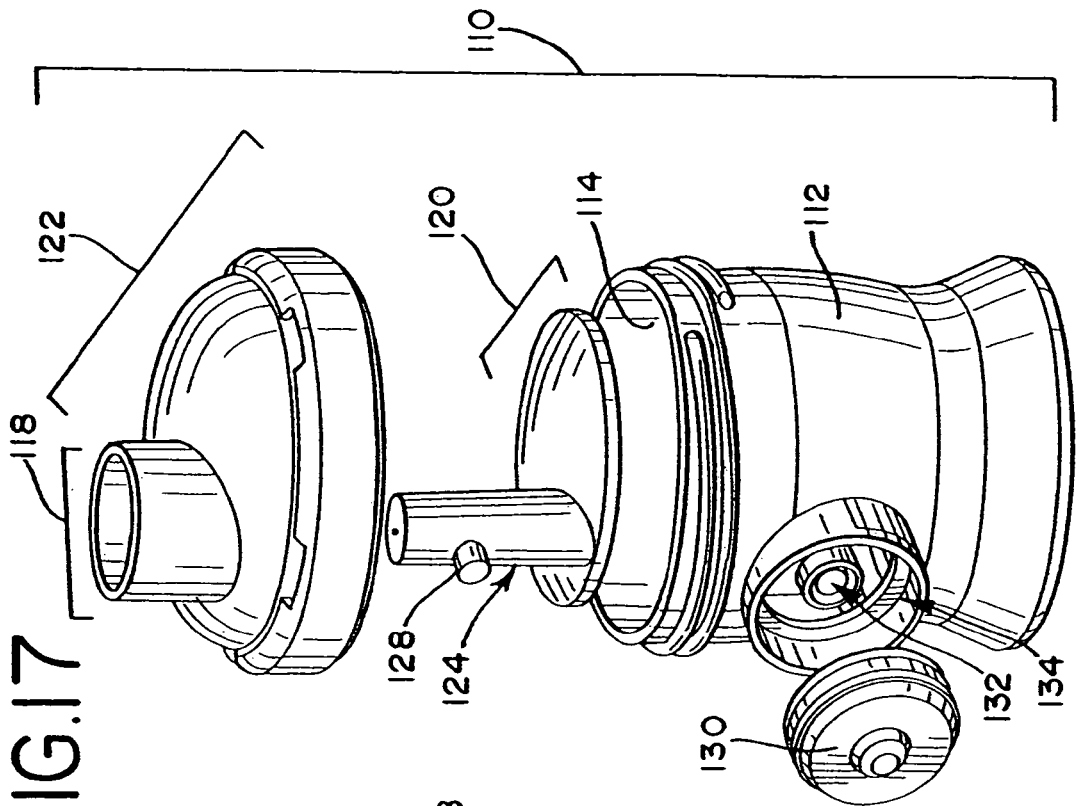
FIG. 17 is an exploded view of a first alternative embodiment of the nebulizer of FIG. 1.

Referring to FIGS. 11, 12 and 13, the contour and topology of the bottom of the chamber may also be varied. In FIG. 11A the chamber floor 80 is flat. A concave chamber floor 81 is illustrated in FIG. 11B. A split angle chamber section 83 connects with a shallow angle section 84 to guide fluid into the steep angle section 83 is shown in FIG. 12. A chamber floor 85 having more than two angled sections is illustrated in FIG. 13.

Figure 16:
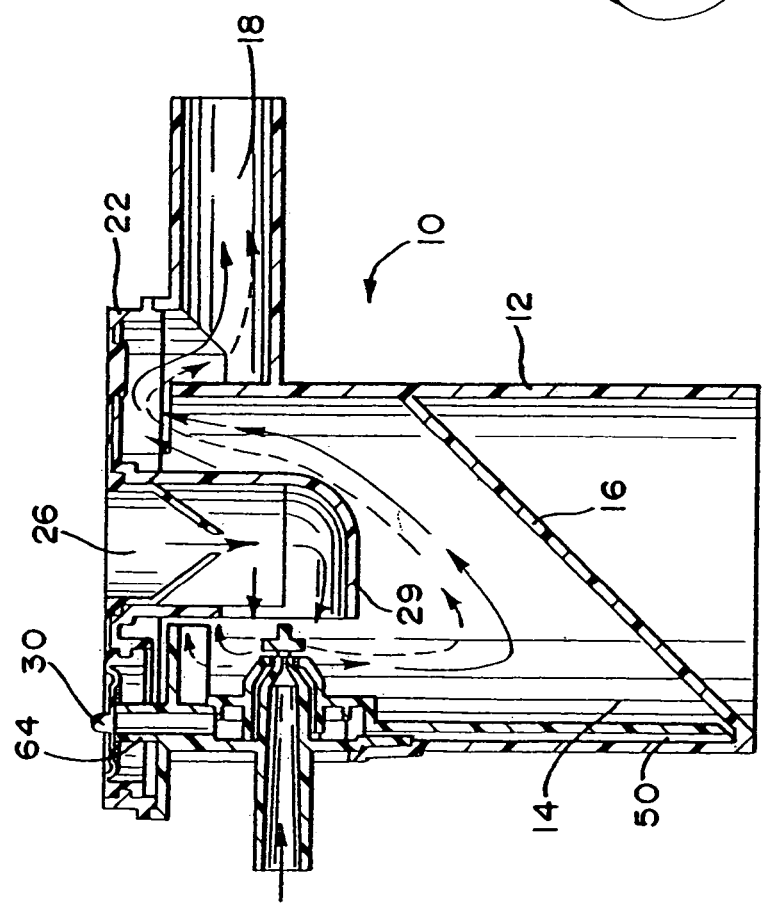
FIG. 16 is a cross-sectional view of the nebulizer of FIG. 1 illustrating gas and aerosol flow and the position of the valves in a fully actuated position.

Referring to FIGS. 14-16, the operation of the nebulizer 10 is described below. The first phase of operation, when the nebulizer is at rest, is illustrated in FIGS. 14A-14C. When the user is passive, such as when the user is between exhalation or inhalation, or when no user is breathing through the air outlet 18, the only flow of air into the chamber 14 is via the gas nozzle where a source of pressurized gas continuously feeds in gas at a predetermined rate. For example, a gas supply may be set up to supply air at a rate of eight liters per minute. As illustrated by the flow arrows in FIG. 14A, the pressurized gas exits the gas orifice, impacts the diverter, and flows around the chamber and over the barrier.

After passing over the barrier 20, the air from the pressurized source exits through the air outlet and any mouth piece attached to the air outlet. During the rest phase, the duck bill valve 26 of the ambient air inlet remains sealed and the exhalation valve also remains sealed. The fluid channel air inlet valve 30, however, remains spaced away from the fluid channel air inlet 64 so that air from within the chamber 14 can cycle through the fluid channel air inlet and between the gas nozzle and nozzle cover out through the fluid orifice 57 as shown in FIG. 14C. The negative pressure that would usually be created by the flow of the pressurized gas over the tip of the fluid orifice is eliminated or significantly reduced by this configuration. Specifically, because air from within the chamber may cycle freely through the fluid channel air inlet and out the fluid orifice, no fluid is drawn up through the fluid channel because no negative pressure is allowed to form over the fluid. As shown in FIG. 14B, air from within the chamber is drawn through the fluid channel air inlet 64 and into the chamber 62 around a portion of the nozzle cover. The air from the chamber 62 then flows through an opening in the bottom of the nozzle cover and out between the nozzle cover and nozzle through the liquid orifice. During the rest phase of the nebulizer, no aerosol is being produced and air is simply being circulated through the fluid channel air inlet and fluid orifice. The overall air pressure inside the nebulizer is slightly positive due to the continual influx of air through the pressurized gas inlet.

At the start of inhalation, the pressurized gas nozzle 52 continues to inject air at a continuous rate, however now the air pressure inside the nebulizer chamber 14 is slightly negative. As shown in FIGS. 15A-15C, the fluid channel air inlet valve 30 reacts to the start of inhalation by flexing downward onto the opening of the fluid channel air inlet to seal against the fluid channel air inlet 64. Once the fluid channel air inlet is sealed off from air within the chamber, a negative pressure forms in the fluid channel 50 and fluid from the reservoir at the bottom 16 of the chamber is drawn up the fluid channel 50 and out to the fluid orifice 57 between the pressurized gas nozzle and the nozzle cover. As shown in FIG. 15B, the fluid is drawn up between the fluid channel stem 58 and the recess 48 in the chamber wall as indicated by the arrow in FIGS. 15B and C. The negative pressure over the fluid is generated by the flow pressurized gas diverted against the diverter 66 over the fluid orifice 57. When fluid reaches the fluid orifice, it is drawn out and mixes with the pressurized gas to form an aerosol. In this embodiment, aerosolization is enhanced by impacting the fluid/gas mixture against the diverter. As shown in FIG. 15A (dotted line indicating liquid/aerosol and solid line indicating gas) the aerosol is formed and travels around the diverter and ambient air inlet, over the barrier and out through the air outlet. Until inhalation proceeds to the point where the negative pressure generated in the chamber by the inhaling patient is greater than the threshold needed to overcome the force holding the lips of the duck bill valve closed, no ambient air will enter through the air inlet. The exhalation valve 28 also remains closed.

As illustrated in FIG. 16, the duck bill valve opens to provide an additional flow of air into the chamber in response to continued inhalation. The air from the ambient air inlet is directed over the gas and liquid orifices to enhance mixture and transport of the aerosol. The membrane of the fluid channel air inlet valve remains sealed over the fluid channel air inlet and liquid continues to be drawn up through the fluid channel and aerosolized in the chamber.

When the patient exhales, the fluid channel air inlet valve 30 responds to the positive pressure in the chamber to separate from the fluid channel air inlet and allow air from within the chamber to again circulate through the fluid channel air inlet in the same manner as shown in FIG. 14B. The duck bill valve 26 seals against the exhalation so that no air exits the ambient air inlet and the exhalation valve 28 opens up to permit the patient's exhalation to exit the chamber. Because the fluid channel air inlet valve separated from the fluid channel air inlet, no fluid is drawn up through the fluid channel and aerosolized during exhalation.

Another preferred embodiment of the nebulizer 110 is illustrated in FIGS. 17-20. In this embodiment, the container 112 is separate from, and threadably attachable to, the lid 122. A chamber 114 is defined within the container between the chamber floor 116 and lid 122. The chamber floor 116 is preferably curved such that the center of the chamber floor is higher than the perimeter so as to direct any liquid toward the perimeter of the chamber floor. A suction plate 120 integrally connected with a nozzle cover 124 is configured to rest directly over the distal end of the pressurized gas nozzle 126 that extends through the chamber floor. A fluid channel 127 is formed by the spacing between the bottom surface of the suction plate 120 and the chamber floor, and the space between the pressurized gas nozzle 126 and the nozzle cover 124. In one embodiment, the suction plate may include one or more small openings to allow passage of fluid from above the suction plate to the fluid channel 127.

As in the embodiment of FIG. 1, the nebulizer 110 of FIGS. 17-20 includes a fluid channel air inlet 128 in communication with the fluid channel 127 and a fluid channel air inlet valve 130 to control actuation of the nebulizer. The fluid channel air inlet 128 extends from the side of the fluid channel 127 toward the distal end of the nozzle cover 124. Preferably, an opening 134 in the side of the chamber 114 adjacent to the nozzle cover and fluid channel air inlet is sized to receive a fluid channel air inlet valve 130 flexibly mounted in the opening of the chamber wall. In one embodiment, the fluid channel air inlet valve is a rolling membrane snap fit into the opening 134 of the chamber wall. An air inlet guide 132 is attached to the container 112 and extends from the edge of the opening 134 so that the fluid channel air inlet 128 is centered in the opening 134 when the nebulizer is assembled.

The lid 122 of the nebulizer defines an air outlet 118 that extends through to the inside of the chamber 114 to a chimney structure 136 having a diverter 138 positioned on the end. Preferably, the threads for the lid and container are such that the diverter aligns directly over the pressurized gas orifice 140 in the chamber. The diverter 138 has a curved surface and is attached to the chimney by several support members 142. In operation, the nebulizer receives a continuous flow of pressurized gas through the gas nozzle and exiting through the gas orifice. At rest, or during exhalation, the fluid channel air inlet valve 130 remains spaced away from the fluid channel air inlet 128 and air inlet guide 132 such that air within the chamber cycles through the fluid channel and out the fluid orifice. Manually, or due to a drop in pressure in the chamber from a patient's inhalation, the fluid channel air inlet valve 130 flexes to cover the proximal end (i.e. the end that is closest to the membrane) of the fluid channel air inlet guide 132 such that the fluid channel air inlet is blocked and a negative pressure generated by the flow of pressurized gas over the liquid orifice generates sufficient negative pressure to draw fluid up the fluid channel 127. This fluid is then mixed with the pressurized gas and directed against the diverter 138 to form an aerosol which may be drawn out through the air outlet. A suitable mouthpiece and exhalation valve that may be adapted to fit to the air outlet 118 are illustrated in U.S. Pat. No. 6,044,841, the entire specification of which is incorporated herein by reference. Alternatively, a mask with an exhalation valve may be adapted to fit the air outlet 118. Suitable masks are disclosed in U.S. Pat. Nos. 5,988,160 and 5,645,049, the entire specifications of which are incorporated by reference herein. As is illustrated in FIGS. 27 and 28 and described in greater detail below, the membrane used to respond to negative pressure to initiate nebulization may also be configured to allow ambient air to flow into the chamber while maintaining a seal against the fluid channel air inlet.

FIGS. 21-22 illustrate another embodiment of a nebulizer 210 similar to the embodiment illustrated in FIGS. 8-11. As shown in FIGS. 21-22, the container of the nebulizer has a pressurized gas inlet 226 that enters into the chamber 214 at a substantially perpendicular orientation to the fluid channel 227. In this embodiment, the fluid channel 227 is formed in a suction tube 224 attached to the suction plate 220 independently of the pressurized gas inlet 226. A fluid channel air inlet extends from the suction tube 224 and is oriented to cooperate with a air inlet guide 232 connected to the container 212. An opening 234 in the chamber wall receives the fluid channel air inlet valve 230. Assembled, the fluid channel air inlet valve 230 and fluid channel air inlet 228 are aligned so that an external force or a negative pressure in the chamber will cause the valve to cover the fluid channel air inlet and allow the fluid in the fluid reservoir on the bottom of the chamber to be drawn up the fluid channel, reach the fluid orifice 236 and mix with pressurized gas entering from the gas orifice 240. Although a separate air inlet valve may be used, preferably the fluid channel air inlet valve is integrated with an ambient air inlet valve feature, as described below and shown in FIGS. 27-28, so that the membrane 230 serves a dual purpose.

Also, as illustrated in FIG. 22 the configuration of the gas orifice 240 and diverter 238 is such that the diverter 238 is a constricted tube having an hour glass-type shape that does not completely block the flow of gas from the gas orifice 240. Instead, the diverter 238 funnels the gas over the fluid orifice 236 so that pressurized gas from the pressurized gas nozzle is channeled over a fluid exit orifice and nebulized as it is drawn into the pressurized gas stream. Thus, unlike the nozzle and diverter configuration of the embodiment in FIGS. 1-4, the pressurized gas flow is not oriented directly against a diverter structure which is spaced apart and directly opposes the flow of the pressurized gas to cause the gas to flow substantially perpendicular to its initial path from the gas orifice.

Alternate gas orifice and diverter structures suitable for use in the embodiment of FIGS. 21-22, or in modified embodiments of the nebulizer of FIGS. 1-4, are shown in FIGS. 22-25. In FIG. 23, the liquid orifice 250 and suction tube 252 are configured to deflect a portion of the pressurized gas flow and no separate baffle or diverter is used. Similarly, in FIG. 24, the gas orifice 256 for the pressurized gas nozzle is not directly obstructed by the diverter 254. Instead, the pressurized gas orifice 256 is positioned off-center in an asymmetric diverter cone 258 away from the side of the diverter in which the fluid orifice 260 is formed.

Another embodiment of a nebulizer 310 is illustrated in FIGS. 25 and 26. In this embodiment, the pressurized gas inlet 326 is formed as part of the lid 322 in parallel with the air outlet 318. A removable fluid channel assembly 327 includes a fitting 350 configured to frictionally fit into the end of the gas inlet 326 extending into the chamber 314. A gas orifice 340 is oriented to direct pressurized gas directly across a fluid orifice 336 positioned adjacent to, and perpendicular to, the gas orifice 340.

As with the embodiments of FIGS. 17-22, the nebulizer 310 preferably utilizes a dual function air inlet valve/fluid channel air inlet valve 330. The valve 330 is retained in an opening 334 in the container 312 and positioned so that the center of the valve 330 aligns with the fluid channel air inlet 328 when the nebulizer 310 is assembled. Although the fluid channel assembly 327 is shown having a tube-like structure that extends to the chamber floor 316, in other embodiments the fluid channel assembly 327 may connect to a suction plate such as discussed above. Also, configurations of fluid and gas orifices other than specifically shown in FIGS. 25 and 26 may be substituted for the configuration shown. It is contemplated that a diverter may also be used in certain configurations of the fluid and gas orifices.

The embodiment of FIGS. 25 and 26 functions substantially similarly to those of FIGS. 17-22. At rest and upon exhalation, the valve 330 remains spaced away from the fluid channel air inlet 328 so that gas from the gas orifice cannot create a sufficient negative pressure in the fluid channel 329 as it passes across the fluid orifice 336 to draw fluid and initiate nebulization. Upon inhalation, the negative pressure in the chamber draws the valve 330 against the fluid channel air inlet to initiate nebulization. As inhalation continues, the outer periphery of the valve 330 rolls inward toward the chamber and pulls away from the opening 334 so that air inlets 338 are revealed and ambient air flows into the chamber.

FIGS. 27-28 illustrate the operation of the air inlet portion of the combination air inlet/fluid channel air inlet valve 230. As illustrated in FIG. 28, upon inhalation the circumferential inlets 250 on the valve 230 adjacent the opening 234 in the chamber wall flex inward to permit passage of ambient air into the chamber while the center of the valve 230 continues to prevent the flow of air into the fluid channel air inlet 228. As shown in FIG. 27, these circumferential inlets 250 reseal to prevent passage of air from the chamber to the outside upon exhalation.

Figure 30:
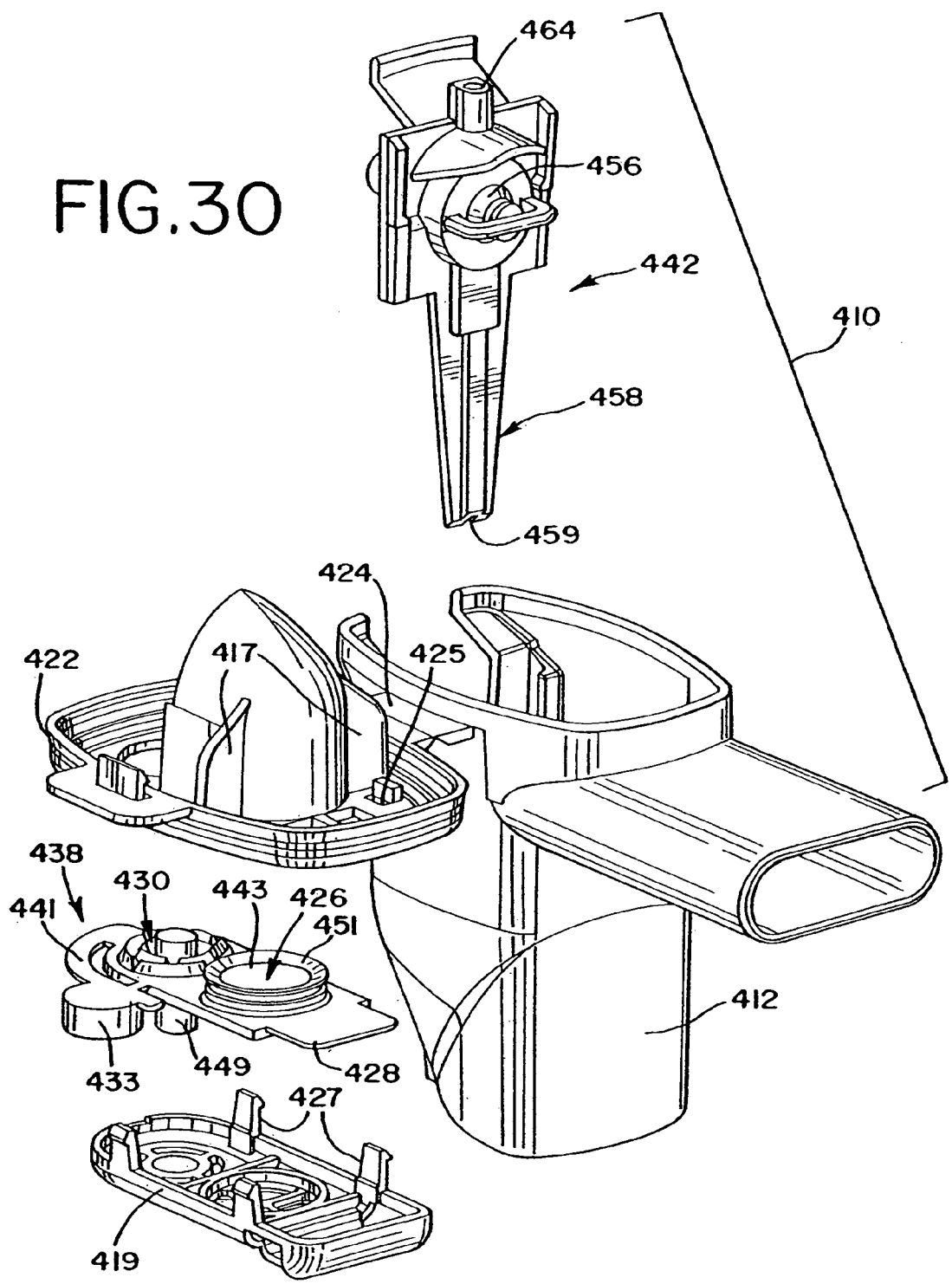
FIG. 30 is an exploded view of the nebulizer of FIG. 29.
Figure 31:
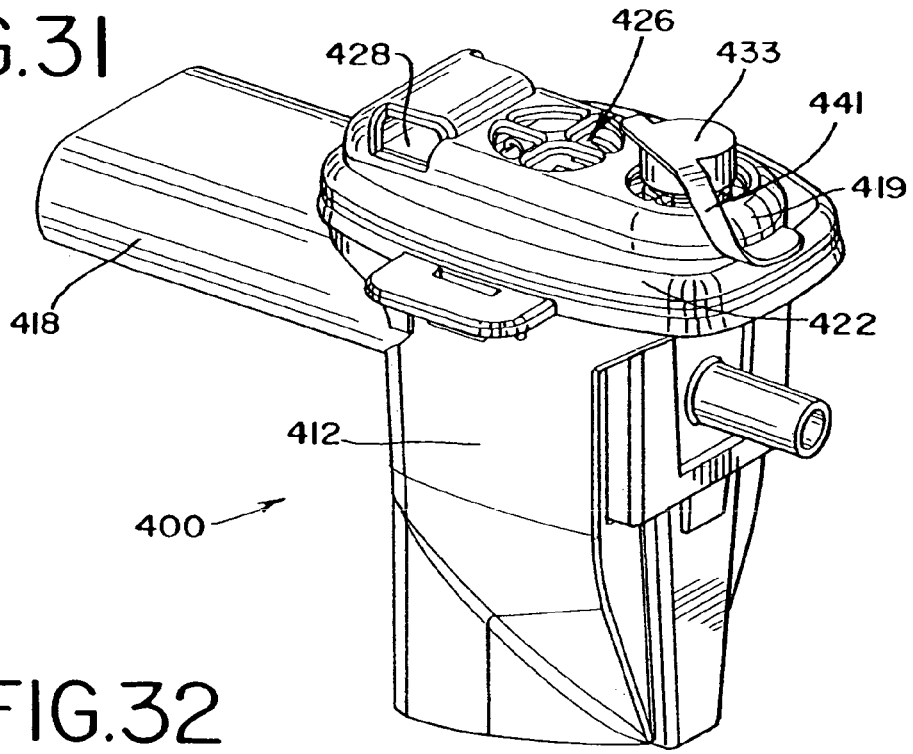
FIG. 31 is a perspective view of the nebulizer of FIG. 29 with a cap positioned to place the nebulizer in a continuous nebulization mode.

FIGS. 29-36 illustrate an alternative embodiment of a nebulizer 410 that is related to the embodiment of FIGS. 1-4. In this embodiment, the nebulizer 410 includes a lid portion 422 connected by a hinge 424 to the housing 412. The lid may be repeatedly sealed to allow for a fluid, or additional fluid, to be placed inside. As in the embodiment of FIGS. 1-4, a series of valves 426, 428 and 430 fit into or across respective openings in the lid portion 422 to facilitate operation of the nebulizer 410. A substantially rigid grid 419, is configured to attach to the lid 422 using a snap-fit or other type of connection mechanism. As shown in FIG. 30, each protrusion 427 on the grid 419 is designed to cooperate with a receptacle 425 on the lid 422. The grid 419 acts to both secure the various valves 426, 428 and 430 onto the lid 422 and protect these valves from abrasion and unintentional contact with fingers or other objects. A series of openings on the grid permit the valves 426, 428 and 430 captured between the grid and the lid portion freedom to move between their respective opened or closed positions as described in greater detail below. The grid may be constructed of the same material as the container 412 or any of a number of other substantially rigid materials.

Figure 32:
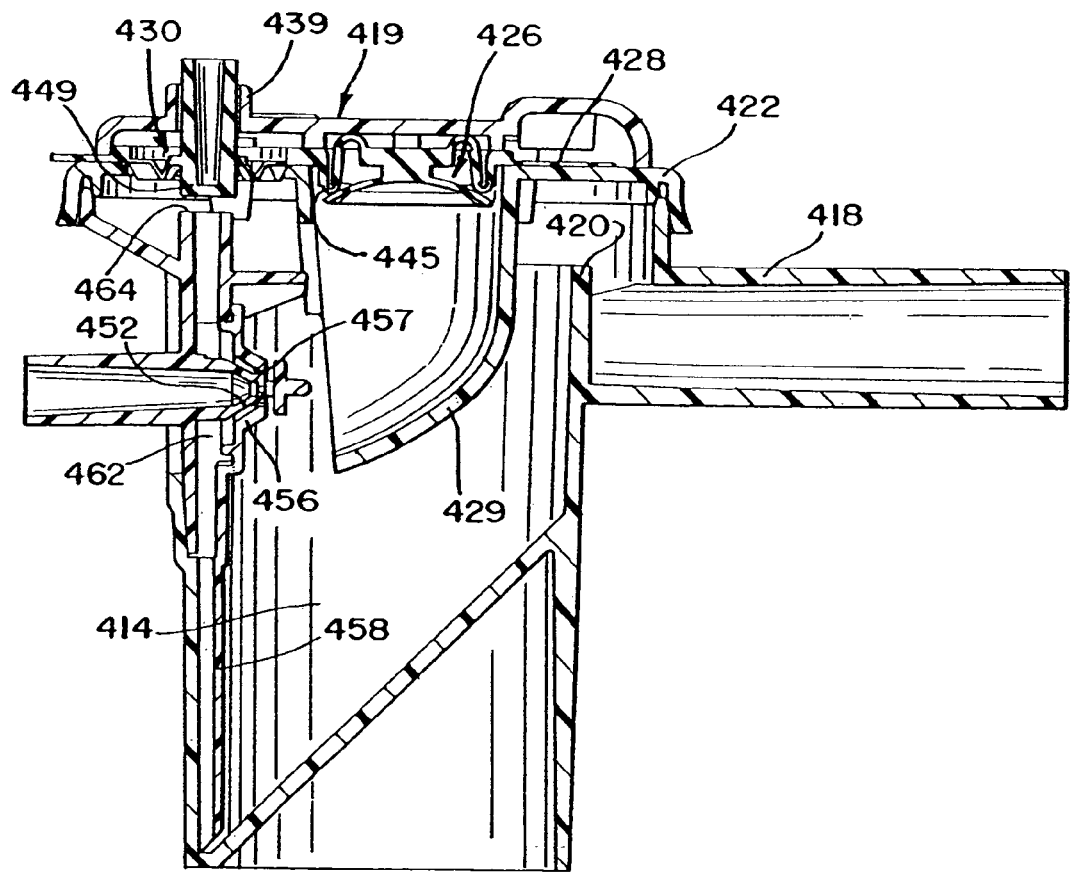
FIG. 32 is a cross-sectional view of the nebulizer of FIG. 29.

The nebulizer of FIGS. 29-36 also includes a cap 433 having an inner diameter sized to form a friction fit around the annular valve guide 439. As will be explained in greater detail below, the cap 433 may be used to manually set the nebulizer to continuously nebulize a fluid present in the container 412 by fitting the cap over the annular valve guide 439 in the grid 419 so that the fluid channel air inlet valve 430 is held down as is shown in FIG. 32. The nebulizer may be returned to its breath actuated configuration by removing the cap 433 and allowing the fluid channel air inlet valve 430 to move freely.

An integrally formed valve system 438 that may be used in the nebulizer 410 is best shown in FIGS. 30 and 33-34. The valve system 438 may include each of the air inlet valve 426, exhalation valve 428 and fluid channel air inlet valve, as well as the cap 433 and tether 441, in a single molded piece. The material used is preferably flexible and resilient. In one embodiment, the material is a flexible rubber material, such as a silicone rubber. Although the individual valves may be fabricated separately on separate pieces of flexible material, or the valves may each be constructed from numerous individual components, the valve system 438 is preferably a one-piece, integrated construction. The cap 433 is shown as connected to the valve system 438 by a tether 441. The cap 441 may be manufactured with one or more pieces of linking material 453 between the cap and the main body of the valve system 438 so that the cap and tether do not become damaged in shipment or get in the way with the operation of the nebulizer 400 if the cap will not be used. The linking material 453 may be manufactured with a thin piece of the same material used for the rest of the valve system so that it may be purposefully cut or torn by a user.

The cap and tether may be fabricated separately from the rest of the valve system or the tether may be eliminated altogether in other embodiments. A separate cap may be used with this embodiment of nebulizer 400 to cause continuous nebulization, or with any of a number of breath actuated nebulizers having externally accessible actuator mechanisms. As shown in FIG. 37, a discrete cap 533 may be sized to fit over the movable indicator/actuator 530 of other breath actuated nebulizers 500, such as those disclosed in U.S. Pat. No. 6,044,841, the entirety of which is incorporated by reference herein. The removable cap acts to manually hold down an actuator to turn the normally breath actuated nebulizer into a continuous nebulizer that will continually nebulize a fluid regardless of whether a patient is inhaling or exhaling. In other embodiments, the cap may be implemented by strap or sleeve sized to both grip the container and fit over the valve or other actuator that controls nebulization of the nebulizer.

Figure 33:
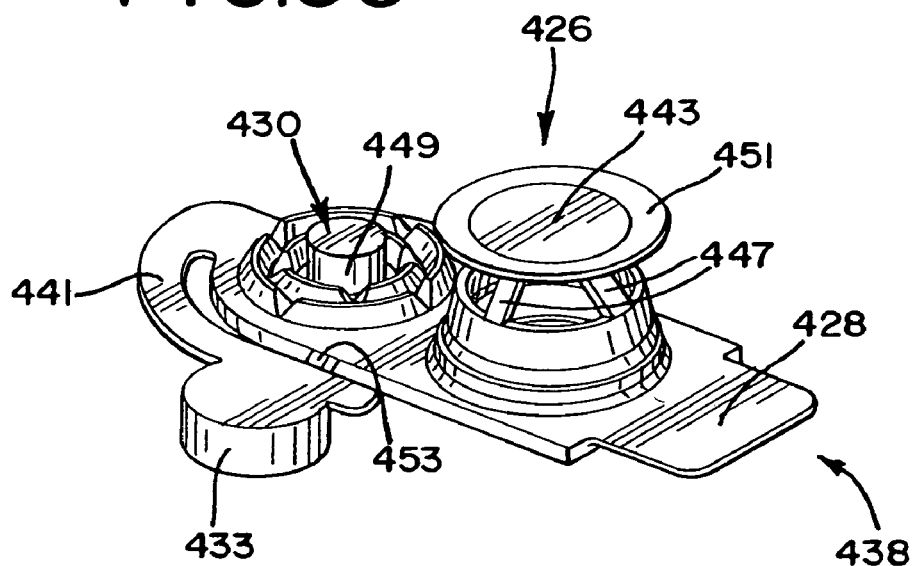
FIG. 33 is a perspective view of a valve system suitable for use in the nebulizer of FIG. 29.
Figure 34:
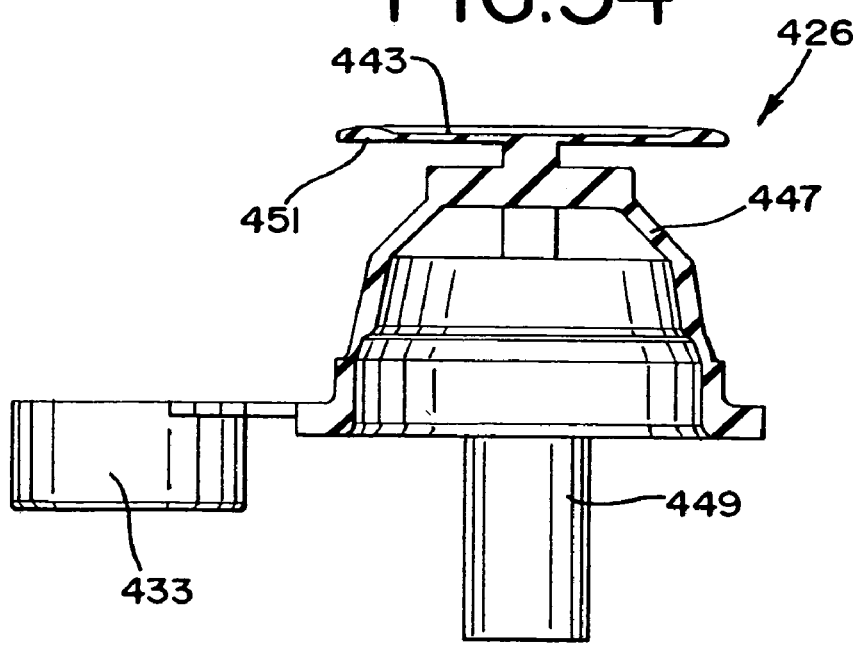
FIG. 34 is a cross-sectional side view of the valve system of FIG. 33.

Referring again to FIGS. 29-36, the air inlet valve 426 in FIGS. 29-34 is an umbrella valve, unlike the duck-bill valve embodiment of FIGS. 1-4. The umbrella valve is preferably manufactured as a single piece within the valve system 438. A thin, flexible hood 443 is connected to the valve seat 445 by spaced apart legs 447. Prior to assembly, the hood 443 and legs 447 are extended as shown in FIG. 33. In preparation for assembly, the hood 443 is pressed down into the valve seat 445 leaving the hood biased close against the valve seat and the legs curled beneath as shown in FIG. 32.

In one embodiment, the hood 443 is 15 millimeters (mm) in diameter with an inner portion extending 11 mm in diameter and having a substantially constant thickness of about 0.25 mm. The outer annular portion 451 of the hood has a bump of increased thickness, of about 0.55 mm, in order to help control deformation of the hood when mounted in the nebulizer and to help reduce noise generated when air is drawn through the valve 426. The legs 447 may be about 5 mm thick in this embodiment. It is also contemplated that the hood 443 may be constructed from a uniform thickness material or a material that is manufactured to contain a variety of thicknesses. The thickness and diameter of the hood 443, and the thickness of the legs 447, may be adjusted as necessary to obtain the desired flexibility and sensitivity to inhaled air. As shown in FIG. 32, the air inlet valve 426 covers the opening in the lid portion 422 over the ambient air guide 429. The hood 443 is oriented toward the interior of the container 412 so that the negative pressure resulting from inhalation through the air outlet will cause the hood to flex away from the valve seat 445 and allow air into the chamber 414.

The fluid channel air inlet valve 430 differs from that of the embodiment of FIGS. 1-4 in that the flexible membrane of the valve 430 carries a centrally located pillar 449 positioned to extend perpendicularly through the surrounding membrane of the valve 430 such that one end of the pillar 449 is positioned above the fluid channel air inlet 464 and the other end extends through the annular valve guide 439 in the grid 419. The fluid channel air inlet valve is configured to deflect over the gap between the end of the pillar and the opening of the fluid air inlet channel, where the gap is preferably in the range of 0.5-2.0 mm, and most preferably approximately 1.3 mm, before it blocks the end of the fluid channel air inlet 464. Other gap distances may be used with variations in the parameters of the membrane, geometry and diameter, and variation in other aspects of the nebulizer such as the size of the fluid channel air inlet.

As with the embodiment of FIGS. 1-4, the fluid channel air inlet valve 430 is designed to be spaced away from the fluid channel air inlet during exhalation and to cover the fluid channel air inlet during air inhalation so that the negative pressure from the continuous gas flow in the gas nozzle will draw fluid up the fluid channel for nebulization. Although responsiveness may be tuned for particular applications, in one embodiment, the fluid channel air inlet valve is designed to respond to a negative pressure of approximately 0.5-1.0 cm H$_2$O to achieve the deflection necessary to cover the fluid channel air inlet 464 and allow fluid to be drawn up for nebulization. The exhalation valve 428 may be a flap of material extending from the edge of the valve system 438 that is thin enough to move away from an opening in the lid 422 during exhalation, and both large enough and rigid enough to seal off that opening during inhalation.

Figure 35:
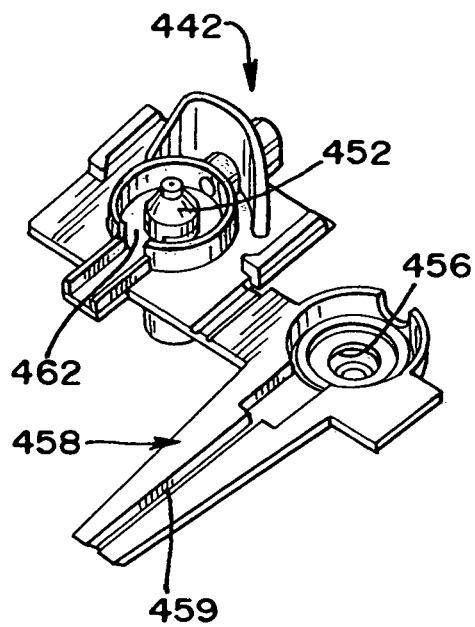
FIG. 35 is a front perspective view of an unassembled nozzle system for use in the nebulizer of FIG. 29.
Figure 36:
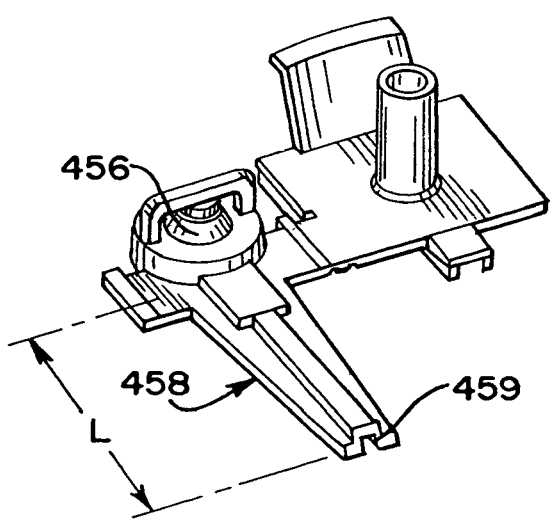
FIG. 36 is a rear perspective view of an unassembled nozzle system for use in the nebulizer of FIG. 29.
Figure 37:
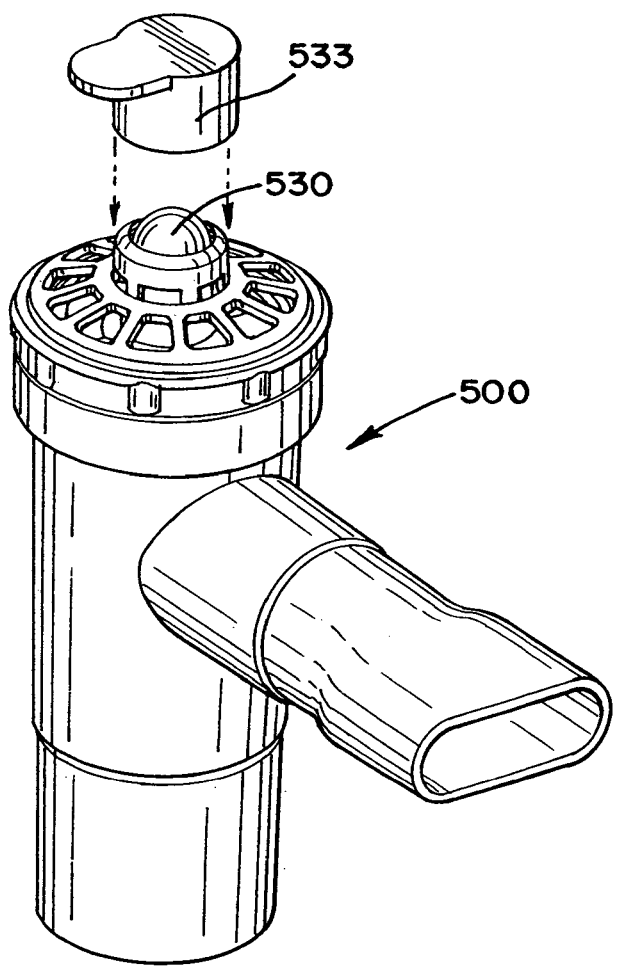
FIG. 37 illustrates a breath actuated nebulizer and removable cap for connecting the breath actuated nebulizer into a continuously nebulizing nebulizer.

The nebulizer 400 embodiment of FIGS. 29-36 also differs from that of FIGS. 1-4 in that a barrier 417 to prevent large droplets from escaping the nebulizer is disposed on the underside of the lid portion 422 adjacent the chimney 429 so that a lower barrier 420 may be used where the air outlet 418 meets the wall of the container 412 to further improve air flow through the outlet 418. In addition, as shown in FIGS. 35-36, the nozzle system 442 differs from that in FIGS. 1-4 in that the nozzle cover 456 does not extend to the base of the gas nozzle 452 so that the fluid chamber 462 opens up and provides less restriction to fluid flow from the lumen formed by the combination of the recessed channel 448 chamber wall and the recessed portion 459 of the fluid channel stem 458. In alternative embodiments, the wall of the nozzle cover 456 may be fabricated at different heights to vary the amount that fluid flow is restricted in the chamber 462. Another difference between the nozzle system 442 shown in FIGS. 35-36 and the nozzle system 42 shown in FIGS. 1-4 is the configuration of the liquid channel formed between the gas nozzle 452 and the nozzle-cover 456 that culminates in the liquid orifice 457 (FIG. 32). Specifically, in the embodiment of FIGS. 35-36, this liquid channel either widens or maintains a constant cross-section from the liquid orifice 457 towards the base of the gas nozzle 452 at the nebulizer container wall, as compared to the cross-section of the liquid channel defined by the nozzle and nozzle cover shown in FIGS. 1-4 that widens in the middle and narrows again at each end.

Also, performance of the nebulizer may be adjusted by narrowing or widening the recessed portion of the fluid channel stem. For example, by narrowing the recessed portion of the stem, the nebulizer efficiency may be improved because less fluid is left in the reservoir when the nebulizer begins to sputter out and thus the amount of fluid required for the nebulizer to produce a desired amount of aerosol may be reduced. In one embodiment, the chamber has a volume of approximately 40-45 milliliters (ml), with a maximum fluid fill volume of 5 ml. In this embodiment, the fluid channel length L is preferably in the range of 20-45 mm and most preferably approximately 35 mm. Depending on any one of a number of variables, such as the viscosity of the fluid in the nebulizer, the cross-sectional area of the end of the channel formed by the recessed portion 459 of the fluid channel stem 458 and the container wall may be in the range of 1-16 square millimeters. Again, any of the above dimensions may be adjusted to tune a particular nebulizer for a specific fluid.

In all of the above-embodiments, a nebulizer capable of both breath actuation and manual actuation has been disclosed where a diverter, gas orifice, and liquid orifice are maintain in a fixed position with one another at all times. Nebulization is initiated by movement of a valve over the fluid channel air inlet that is in communication with the fluid channel linking the liquid orifice with the reservoir in the chamber. By using a flexible membrane as the fluid channel air inlet valve, a very fast and reliable response to both increased and decreased pressures within the chamber of the nebulizer may be realized. As illustrated in the embodiments of FIGS. 1-7 and 29-36, this design may be used to simplify and reduce the number of components needed to assemble a nebulizer. As few as three separate molded assemblies may be snapped fit together without the need for any separate fasteners. Further, no separate spring biasing members or any type of metal component is necessary in the design of a nebulizer according to a preferred embodiment. Additionally, a variety of fluid channel configurations may be utilized with the fluid channel air inlet and fluid channel air inlet valve design discussed herein. As described above, the fluid channel may be a separate element from the pressurized gas nozzle or may be formed in cooperation with the pressurized gas nozzle. Similarly, the fluid channel may be contained in a single component of the nebulizer or formed from the mating of more than one assembly in the nebulizer.

It is intended that the foregoing detailed description be regarded as illustrative rather than limiting, and that it be understood that the following claims, including all equivalents, are intended to define the scope of this invention.

We claim:

1. A nebulizer comprising:
a housing having an ambient air inlet and a chamber for holding an aerosol;
an air outlet communicating with the chamber for permitting the aerosol to be withdrawn from the chamber;

a pressurized gas inlet adjacent a fluid orifice, the pressurized gas inlet in communication with the chamber and the fluid orifice in communication with a fluid channel, wherein an end of the fluid channel is positioned in a fluid reservoir in the chamber; and, a fluid channel air inlet valve movably disposed across a fluid channel air inlet, wherein the fluid channel air inlet is in communication with the fluid channel and is positioned between the fluid reservoir and the fluid orifice.

2. The nebulizer of claim 1, further comprising a diverter positioned in the chamber adjacent to the pressurized gas inlet.

3. The nebulizer of claim 2, wherein the fluid channel air inlet valve comprises a flexible membrane.

4. The nebulizer of claim 3, wherein the flexible membrane comprises an elastomer.

5. The nebulizer of claim 3, wherein the flexible membrane comprises one of silicone and rubber.

6. The nebulizer of claim 2, wherein the ambient air inlet comprises an ambient air inlet valve.

7. The nebulizer of claim 6, wherein the ambient air inlet valve comprises a one-way valve positioned to permit an intake of ambient air into the chamber and prevent an escape of air from the chamber.

8. The nebulizer of claim 7, wherein the ambient air inlet valve comprises a duck-bill valve.

9. The nebulizer of claim 7, wherein the ambient air inlet valve comprises an umbrella valve.

10. The nebulizer of claim 2, wherein the fluid orifice comprises an opening defined by an outer diameter of the pressurized gas inlet and an inner diameter of an end of a pressurized gas inlet cover.

11. The nebulizer of claim 10, wherein the diverter and the pressurized gas inlet are spaced apart at a fixed distance and the diverter is positioned to redirect a flow of pressurized gas at a substantially perpendicular direction from an initial direction of the flow of pressurized gas from the pressurized gas inlet.

12. The nebulizer of claim 10, wherein the pressurized gas inlet comprises a cone-shaped nozzle and the pressurized gas inlet cover comprises a cone-shaped sleeve coaxially positioned around the cone-shaped nozzle.

13. The nebulizer of claim 1, wherein the pressurized gas inlet is oriented perpendicular to the fluid orifice.

14. The nebulizer of claim 1, wherein the fluid orifice is in communication with a fluid reservoir positioned inside the nebulizer.

15. A nebulizer for providing an aerosol to an inhaling patient, the nebulizer comprising:

a housing having an air inlet and a chamber for holding the aerosol;

an air outlet communicating with the chamber for permitting the aerosol to be withdrawn from the chamber;

a pressurized gas inlet located in the chamber;

a fluid orifice located in the chamber adjacent the pressurized gas inlet, the fluid orifice in communication with a fluid channel and in a fixed position relative to the pressurized gas inlet, wherein an end of the fluid channel is positioned in a fluid reservoir in the chamber; and a fluid channel air inlet valve movably disposed across a fluid channel air inlet, wherein the fluid channel air inlet is in communication with the fluid channel and is positioned between the fluid reservoir and the fluid orifice.

16. The nebulizer of claim 15, further comprising a diverter positioned adjacent the pressurized gas inlet and in a fixed position relative to the pressurized gas inlet.

17. A nebulizer comprising:

a housing having an ambient air inlet and a chamber for holding an aerosol;

an air outlet communicating with the chamber for permitting the aerosol to be withdrawn from the chamber;

a pressurized gas inlet adjacent a fluid orifice, the pressurized gas inlet in communication with the chamber and the fluid orifice in communication with a fluid channel, wherein an end of the fluid channel is positioned in a fluid reservoir in the chamber; and, a fluid channel air inlet valve movably disposed across a fluid channel air inlet defined by the fluid channel and positioned between the fluid orifice and the fluid reservoir, and wherein when the fluid channel air inlet is sealed by the fluid channel air inlet valve, nebulization is enabled and when the fluid channel air inlet is unsealed nebulization is disabled.

18. The nebulizer of claim 17, further comprising a diverter positioned in the chamber adjacent to the pressurized gas inlet.

19. The nebulizer of claim 18, wherein the fluid channel air inlet valve comprises a flexible membrane.

20. The nebulizer of claim 19, wherein the flexible membrane comprises an elastomer.

21. The nebulizer of claim 17, wherein the fluid channel air inlet valve is movable in response to a pressure from an object external to the nebulizer.

22. The nebulizer of claim 17, wherein the fluid channel air inlet valve is movable in response to an inhalation through the air outlet.

* * * * *